(12) United States Patent
Sullivan et al.

(10) Patent No.: US 9,568,471 B2
(45) Date of Patent: Feb. 14, 2017

(54) *PLASMODIUM* DIAGNOSTIC ASSAY DEVICE

(75) Inventors: David J. Sullivan, Baltimore, MD (US); Peter Scholl, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1432 days.

(21) Appl. No.: 11/883,130

(22) PCT Filed: Jan. 25, 2006

(86) PCT No.: PCT/US2006/002678
§ 371 (c)(1),
(2), (4) Date: Jul. 17, 2008

(87) PCT Pub. No.: WO2006/081308
PCT Pub. Date: Aug. 3, 2006

(65) Prior Publication Data
US 2009/0117602 A1    May 7, 2009

Related U.S. Application Data

(60) Provisional application No. 60/646,893, filed on Jan. 25, 2005.

(51) Int. Cl.
   *C12Q 1/44*     (2006.01)
   *C12Q 1/02*     (2006.01)
   *C12Q 1/32*     (2006.01)
   *G01N 33/569*   (2006.01)

(52) U.S. Cl.
   CPC ... *G01N 33/56905* (2013.01); *G01N 2333/445* (2013.01)

(58) Field of Classification Search
   USPC ......... 435/7.22, 7.2, 7.1, 7.9, 7.92; 436/543, 436/541
   See application file for complete search history.

(56) References Cited

U.S. PATENT DOCUMENTS

| 4,419,453 | A | * | 12/1983 | Dorman et al. | 436/534 |
| 5,296,382 | A | * | 3/1994 | Wellems et al. | 436/501 |
| 5,665,552 | A | * | 9/1997 | Maret | C07K 16/205 435/34 |
| 5,733,740 | A | * | 3/1998 | Cover et al. | 435/7.32 |
| 6,090,611 | A | * | 7/2000 | Covacci et al. | 435/252.3 |

OTHER PUBLICATIONS

Jelinek et al. J. Clin. Microbiol. 37: 721-723, 1999.*
Genton et al. Southeast Asian J. Trop. Med. Public Health 29: 35-40, 1998.*
Gene ID 813504 updated in Sep. 2010.*
Beadle et al. Lancet 343: 564-568, 1994.*
Genton et al. J. Trav. Med. 3: 172-173, 1996.*
Kumar et al. Indian J. Malariology 33: 166-172, 1996.*
Pinto et al., JAPI, 47(11) (1999).
Iqbal et al., Am. J. Trop. Med. Hyg., 64(1,2):20-23 (2001).
Ardeshir et al., Mol. Biochem. Parasitol., 40:113-128 (1990).
Desakorn et al., Trans. R. Soc. Trop. Med. Hyg., 91(4):479-483 (1997).
Palmer et al., J. Clin. Microbiol., 36(1):203-206 (1998).
Richter et al., Parasitol. Res., 94:384-385 (2004).
Moody, Clin. Microbiol. Rev., 15(1):66-78 (2002).
Stahl et al., Nucleic Acid Res., 14(7):3089-3102 (1986).

* cited by examiner

*Primary Examiner* — S. Devi
(74) *Attorney, Agent, or Firm* — Mintz Levin Cohn Ferris Glovsky and Popeo, P.C.; Peter F. Corless; Richard B. Emmons

(57) ABSTRACT

This invention relates to assays for a *Plasmodium* analyte in a liquid sample such as a body fluid. More particularly, the invention relates to a method and apparatus for the detection of a ligand in a body fluid such as urine or blood, which can diagnose malarial infection.

4 Claims, 16 Drawing Sheets

Figure 3
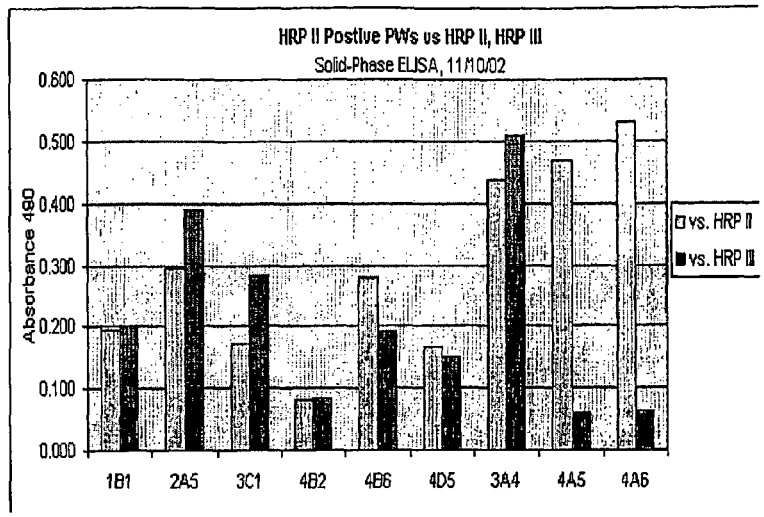
Native
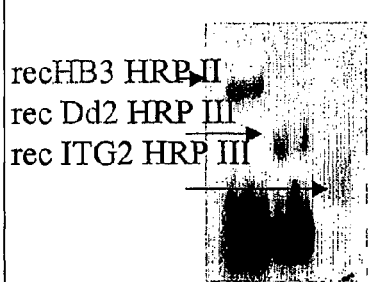
Recombinant
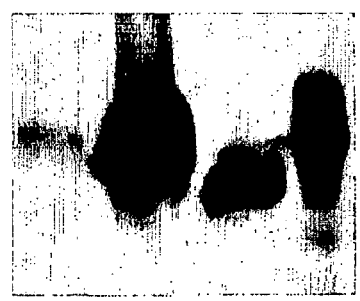
HRP II
7G8  FCR  W2  V1/5
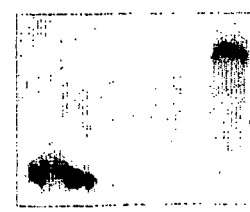
D10   Dd2
HRP III

*4a5 antibody recognizes rHRP II but not rHRP III when used as Primary Ab for Indirect ELISA 3a4 antibody recognizes both rHRP II and rHRP III when used as Primary Ab for Indirect ELISA HB3 II (ng) per well Lanes; 1 Pv (D19), 2 Pf (3d7), 3 *P. yoelii*, 4 *P. knowlesi*,
5. *P. brasilaneum*, 6. *P. Ovale*, 7. Pv (D73) 8. *P. chabaudi*

Figure 8

PfHRP II
MVSFSKNKVLSAAVFASVLLLDNNNSAFNNNLCSKNAKGLNLNKRLLHETQAH
VDDAHHAHHVAD<u>AHHAHHAAD</u>AHHAHHAADAHHAHHAADAHHAHHAADA
HHAHHAAYAHHAHHAADAHHAHHASD<u>AHHAAD</u>AHHAAYAHHAHHAADAHH
AHHASDAHHAADAHHAAYAHHAHHAADAHHAADAHHATDAHHAHHAADAR
HATDAHHAADAHHATDAHHAADAHHAADAHHATDAHHAADAHHATDAHHA
ADAHHAADAHHATDAHHAHHAADAHHAAAHHATDAHHATDAHHAAAHHEA
ATHCLRH

PfHRP III
MVSFSKNKILSAAVFASVLLLDNNNSEFNNNLFSKNAKGLNSNKRLLHESQAHA
GDAHHAHHVAD<u>AHHAHHAAN</u>AHHAANAHHAANAHHAANAHHAANAHHAA
NAHHAANAHHAANAHHAANAHHAANAHHAANAHHAANAHHAANAHHAAN
AHHAAN<u>AHHAAD</u>ANHGFHFNLHDNNSHTLHHAKANACFDDSHHDDAHHDGA
HHDDAHHDGAHHDDAHHDGAHHDDAHHDGAHHDDAHHDGAHHDGAHHDG
AHHNATTHHLHH

MONOCLONAL 3A4

Up close of frozen archival urine test

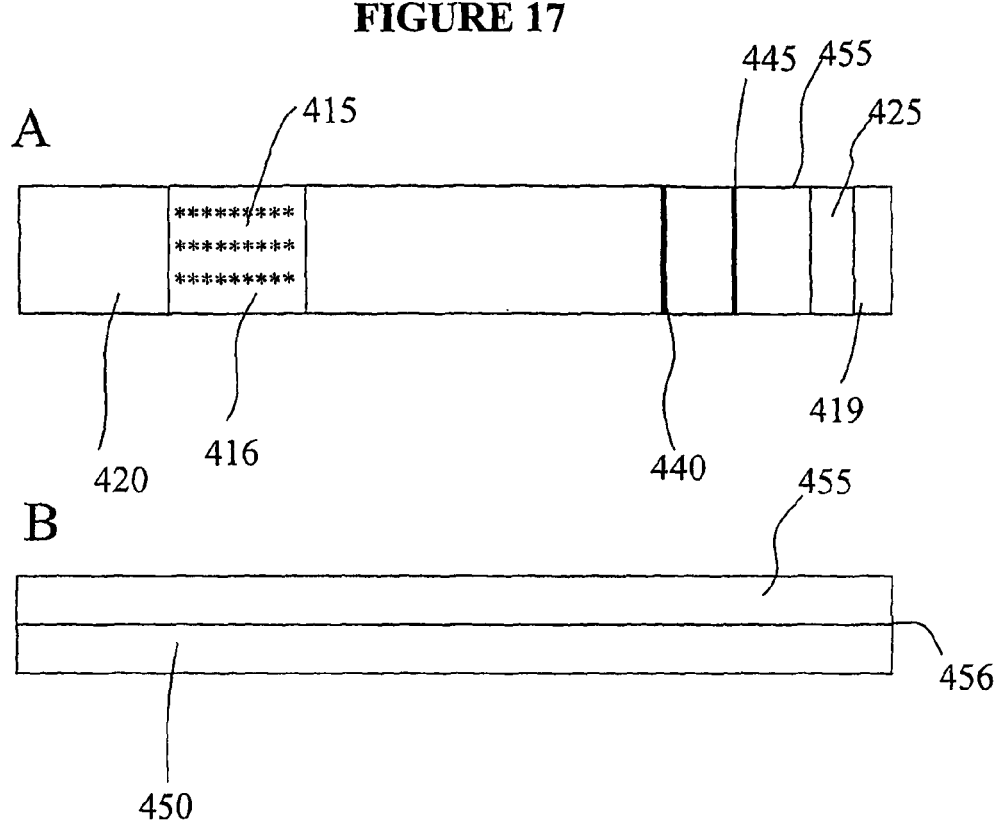
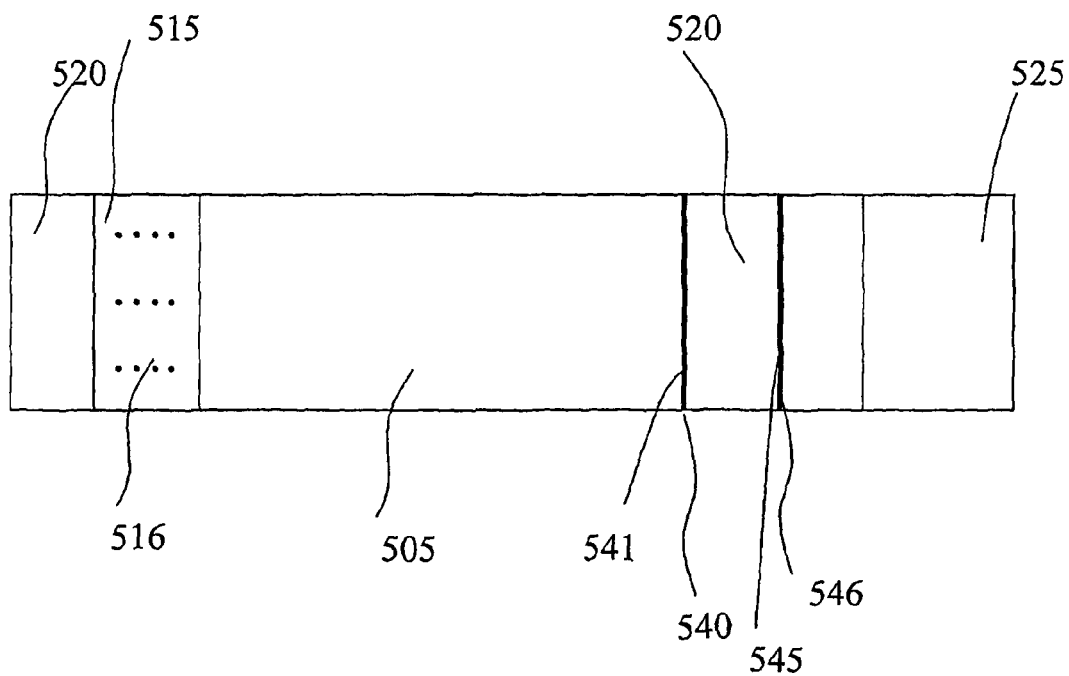

*PLASMODIUM* DIAGNOSTIC ASSAY DEVICE

RELATED APPLICATIONS

This application claims priority to US Provisional Patent Application Ser. No. 60/646,893, entitled "Malaria Diagnosis in Urine," filed Jan. 25, 2005, and is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Nov. 23, 2010, is named 64761716.txt and is 7,815 bytes in size.

BACKGROUND OF THE INVENTION

Malaria kills over 2.7 million people annually amongst the 300-500 million clinical cases worldwide. Malaria is increasingly imported into countries where it is non-endemic and there is an increase in the emergence of drug resistant strains. Malaria predominantly occurs in resource-poor tropical populations where diagnostic capabilities are inadequate. The gold standard blood film malaria diagnostic assay relies on phlebotomy and technical expertise. However, in impoverished populations, the lack of resources to safely draw blood increases the risk of transmitting diseases such as hepatitis B and HIV. Thus, simple assays are much needed in the art to improve the availability of malaria diagnosis to obviate the occupational hazards involved in phlebotomy, to provide better treatment options to those in need, and to differentiate between symptomatic and asymptomatic disease.

It is an object of this invention to provide a rapid, sensitive method for detecting *Plasmodium* analytes in body fluids. Another object is to provide an assay that has high sensitivity.

SUMMARY

This invention relates to assays for analytes in a liquid sample such as a body fluid. More particularly, the invention relates to a method and apparatus for the detection of a *Plasmodium* ligand in a body fluid such as urine or blood.

In one aspect, methods of diagnosing a *Plasmodium* infection in a subject comprise detecting the presence or absence of one or more poly asparagine proteins or fragments thereof in a biological sample of subject.

In one embodiment, the poly asparagine proteins comprise from between about 6 to about 25 consecutive asparagine amino acid residues.

In a further embodiment, the poly asparagine proteins one or more of the proteins listed in Table 1.

In one aspect, methods of diagnosing a *Plasmodium* infection in a subject, comprise detecting the presence or absence of HRP II, HRP III and aldolase or fragments thereof in a biological sample of subject.

In one embodiment, the biological sample is blood, serum, nasal fluid, urine, sweat, plasma, semen, cerebrospinal fluid, tears, pus, amniotic fluid, saliva, lung aspirate, gastrointestinal contents, vaginal discharge, urethral discharge, chorionic villi specimens, skin epithelia, genitalia epithelia, gum epithelia, throat epithelia, hair, or sputum.

In one embodiment, if the sample is urine, buffering the sample to a pH of between about 4 to about 9.

In a further embodiment, if the sample is urine, buffering the sample to a pH of about 7.5 to about 8.5.

In one embodiment, the methods may further comprise detecting the presence or absence of one or more additional *Plasmodium* proteins or fragments thereof.

In one embodiment, the one or more additional proteins comprise histidine rich protein II (HRP II, HRP III), aldolase, lactate dehydrogenase, one or more poly-asparagine proteins or fragments or variants thereof.

In yet another embodiment, the *Plasmodium* is one or more of *Plasmodium falciparum, Plasmodium yoelii, Plasmodium knowlesi, Plasmodium brasilaneum, Plasmodium ovale, Plasmodium chabaudi, Plasmodium vivax, Plasmodium malariae, Plasmodium berghei, Plasmodium reichenowi, Plasmodium gallinaceum*.

In one aspect, methods of differentially diagnosing symptomatic *Plasmodium* infection from asymptomatic *Plasmodium* infection and no infection, comprise detecting the presence or absence of one or more of HRP II, HRP III, poly asparagine proteins or aldolase or fragments thereof in a biological sample of subject with a lateral flow device, and correlating a lack of detection of HRP II, HRP III, poly asparagine proteins or aldolase or fragments thereof with asymptomatic disease or no infection.

In one aspect, methods of differentially diagnosing symptomatic *Plasmodium* infection from asymptomatic *Plasmodium* infection and no infection, comprise detecting the level of one or more of HRP II, HRP III, poly asparagine proteins or aldolase or fragments thereof in a biological sample of subject with a lateral flow device, and correlating a low level or lack of detection of HRP II, HRP III poly asparagine proteins or aldolase or fragments thereof with asymptomatic disease or no infection.

In one embodiment, the detecting is with a lateral flow device, mass spectrometry, immunoassay, or colorimetric assay.

In yet another embodiment, the immunoassay selected from one or more of ELISA, immunoprecipitation, immunodiffusion, radioimmunoassay, immunofluorescence, or lateral flow assay.

In one aspect, methods of detecting the presence of a *Plasmodium* analyte in a sample, comprise applying a sample to an assay device, wherein the assay device comprises a sample receiving membrane which conducts flow of a liquid sample in flow contact with an analyte detection membrane which conducts flow of the sample, wherein the analyte detection membrane comprises a conjugate forming membrane comprising a mobile labeling reagent at a labeling situs, and an immobile capture reagent at a capture situs, wherein the labeling reagent is capable of forming a complex with a poly-asparagine protein or a fragment or variant thereof and the capture reagent is capable of binding a poly-asparagine protein-labeling reagent complex, wherein said liquid sample flows from the sample receiving membrane and mixes with the mobile labeling reagent to move the mobile labeling reagent toward the control situs, and observing a result of the assay.

In one embodiment, the poly asparagine protein is one or more of the proteins listed in Table 1.

In one embodiment, the flow is lateral flow.

In a further embodiment, the assay device further comprises a second mobile labeling reagent at the labeling situs, and a second immobile capture reagent at the capture situs, wherein the second mobile labeling reagent is capable of forming a complex with HRP II, HRP III or a fragment or variant thereof and the capture reagent is capable of binding HRP II, HRP III-labeling reagent complex.

In one embodiment, the methods may further comprise a second mobile labeling reagent at the labeling situs, and a second immobile capture reagent at the capture situs, wherein the second mobile labeling reagent is capable of forming a complex with aldolase or a fragment or variant thereof and the capture reagent is capable of binding aldolase-labeling reagent complex.

In yet another embodiment, the assay device further comprises a second mobile labeling reagent at the labeling situs, and a second immobile capture reagent at the capture situs, wherein the second mobile labeling reagent is capable of forming a complex with lactate dehydrogenase or a fragment or variant thereof and the capture reagent is capable of binding lactate dehydrogenase-labeling reagent complex.

In one aspect, methods of detecting the presence of a *Plasmodium* analyte in a sample, comprise applying a sample to an assay device, wherein the assay device comprises a sample receiving membrane which conducts flow of a liquid sample in flow contact with an analyte detection membrane which conducts flow of the sample, wherein the analyte detection membrane comprises a conjugate forming membrane comprising a first and a second mobile labeling reagent at a labeling situs, and a first and a second immobile capture reagent at a capture situs, wherein the first labeling reagent is capable of forming a complex with a HRP II, HRP III or a fragment or variant thereof; the second labeling reagent is capable of forming a complex with a poly asparagine protein, aldolase, or lactate dehydrogenase; the first capture reagent is capable of binding a HRP II, HRP III-labeling reagent complex; and the second capture reagent is capable of binding a poly asparagine protein, aldolase, or lactate dehydrogenase—labeling reagent complex, wherein said liquid sample flows from the sample receiving membrane and mixes with the mobile labeling reagent to move the mobile labeling reagent toward the control situs, and observing a result of the assay.

In a further embodiment, the poly asparagine protein is one or more of the proteins listed in Table 1.

In one embodiment, an accumulation of particles at the capture situs produces an indicative signal of the presence of the *Plasmodium* analyte in the sample.

In one aspect, assay devices for detection of the presence or absence of a *Plasmodium* analyte in a sample comprise (a) a sample receiving membrane which conducts flow of a sample, and in flow contact with, and (b) an analyte detection membrane which conducts flow of the sample comprising a conjugate forming membrane comprising a first and a second mobile labeling reagent at a labeling situs and a first and a second immobile capture reagent at a capture situs, wherein the labeling reagents are capable of forming complexes with HRP II, HRP III and a poly-asparagine protein, aldolase, or lactate dehydrogenase and the capture reagent is capable of binding an HRP II, HRP III and a poly-asparagine protein, aldolase, or lactate dehydrogenase-labeling reagent complex.

In yet another embodiment, the poly asparagine protein is one or more of the proteins listed in Table 1.

In one embodiment, the flow contact between the sample receiving membrane and analyte detection membrane is lateral flow contact.

In a further embodiment, the back of the sample receiving membrane and the analyte detection membrane are laminated with a semi-rigid material.

In one embodiment, the sample is blood, serum, nasal fluid, urine, sweat, plasma, semen, cerebrospinal fluid, tears, pus, amniotic fluid, saliva, lung aspirate, gastrointestinal contents, vaginal discharge, urethral discharge, chorionic villi specimens, skin epithelials, genitalia epithelials, gum epithelials, throat epithelials, hair, or sputum.

In one embodiment, the sample receiving membrane and the analyte detection membrane are enclosed in a housing.

In one embodiment, the housing comprises a sample application aperture and an observation window positioned to display the immobile capture situs and control situs.

In one embodiment, the devices may further comprise an absorbent sink in lateral flow contact with the analyte detection membrane.

In one embodiment, the devices may further comprise a control reagent immobilized at a control situs.

In a further embodiment, the control reagent comprises an anti-mouse IgG, an anti-goat IgG, an anti-cow IgG, anti-rabbit IgG, or an anti-rat IgG.

In one embodiment, the control reagent is immobilized between the immobile capture reagent and an end of the analyte detection membrane.

In one aspect, kits comprise an assay device comprising (a) a sample receiving membrane which conducts flow of a sample, and in flow contact with, (b) an analyte detection membrane which conducts flow of the sample comprising a conjugate forming membrane comprising a first and a second mobile labeling reagent at a labeling situs and a first and a second immobile capture reagent at a capture situs, wherein the labeling reagents are capable of forming complexes with HRP II, HRP III and a poly-asparagine protein, aldolase, or lactate dehydrogenase and the capture reagent is capable of binding an HRP II, HRP III and a poly-asparagine protein, aldolase, or lactate dehydrogenase-labeling reagent complex; and instructions for use.

Preferably, the back of the sample receiving membrane and the analyte detection membrane are laminated with a semi-rigid material. The semi-rigid material may be at least 0.005 inches thick to produce a device with adequate mechanical strength in the absence of a plastic casing. In a related embodiment, the sample receiving membrane and the analyte detection membrane are enclosed in a housing. The housing, may have a sample application aperture and an observation window positioned to display the immobile capture situs and control situs.

In a further embodiment, the device further comprises an absorbent sink in lateral flow contact with the analyte detection membrane.

In yet another embodiment, the device further comprises a control reagent immobilized at a control situs.

Another aspect of the invention is a kit comprising an assay device as described above and instructions for use.

Other embodiments of the invention are disclosed infra.

BRIEF DESCRIPTION OF THE DRAWINGS

FIG. 3 depicts monoclonal HRP II and HRP III antibody that detects both HRP II and HRP III (clone 3A4 deposited as PTA-123432 on 10 Aug. 2016 at ATCC, 10801 University Boulevard, Manassas, Va. 20110-2209) and another that is more specific to HRP II (clone 4A5 deposited as PTA-123433 on 10 Aug. 2016 at American Type Culture Collection, 10801 University Boulevard, Manassas, Va. 20110-2209). A. ELISA to HRP II and HRP III. B. Western blot probed with 3A4 to cultured parasites clones 3D7 and HB3. C. recombinant HRP II and HRP III as marked with arrows and the repetitive motif (SEQ ID NOS 7 and 8, respectively, in order of appearance) in lower left two lanes as in legend probed with antibody 3A4 D. Additional parasite clones with HRP II in top and HRP III only in bottom.

FIG. 8 shows representative sequence of HRP II (SEQ ID NO: 5) and III (SEQ ID NO: 6). The number of repeat units varies but common 6 amino acid residues such as AHHAH-HAA (SEQ ID NO: 1) or AHHAAD (SEQ ID NO:2) are in both HRP II or III. The epitope seen by different HRP II/III antibodies will vary. For instance AHHAHHAAD (SEQ ID NO: 3) or AHHAAD (SEQ ID NO: 2) appears infrequently with HRP III.

FIG. 17A depicts a top view and 17B depicts side view of a device according to the invention.

FIG. 18 depicts a top view of a device according to the invention.

DETAILED DESCRIPTION OF THE INVENTION

Figure 1:
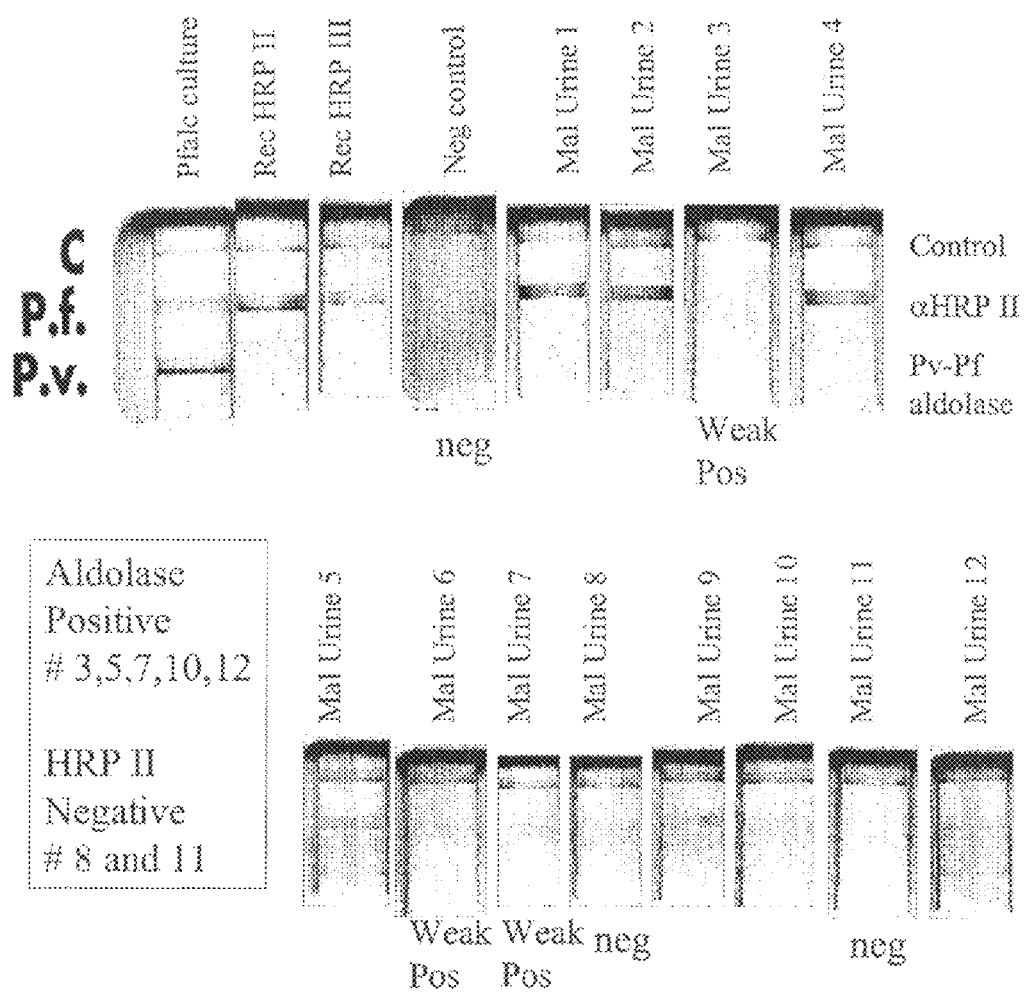
FIG. 1 depicts the immunochromatographic analysis using a blood based test of 12 urine samples from individuals infected with *P. falciparum*. The urine was buffered to pH 8 before analysis of 15 microliters. Urine positive for *P. falciparum* histidine-rich protein (HRP) II in 10 of 12 samples and positive for aldolase in 5 of 12 samples. Urine positive for blood-Mal urine 1 only; Urine ketones positive-sample Mal urine 1, 2, 4, 8, 9, 10, 11. Protein is 1-2+ for all samples except mal urine 7, which was more dilute. Positive controls were *P. falciparum* culture and recombinant HRP II and III and a malaria nonendemic negative control. HRP II and aldolase can be detected in urine.

Disclosed herein are assay devices to determine the presence or absence of a *Plasmodium* analyte in a sample. Further disclosed herein are methods for determining the presence or absence of a *Plasmodium* analyte in a sample. The devices and methods of this invention provide safe and accurate diagnostic tests for malaria.

Broadly, the devices and methods of the invention can be used to detect *Plasmodium* analytes that may be assayed using known immunoassay procedures, or known to be detectable by such procedures, using antibodies or other proteins comprising binding sites for analytes. Various specific assay protocols, reagents, and analytes useful in the practice of the invention are found, for example, in U.S. Pat. No. 4,313,734, and U.S. Pat. No. 4,366,241.

As used herein, the term, "analyte" is intended to refer to any component of a sample (e.g., molecule, compound, or aggregate thereof) to be detected and optionally quantitatively determined by an assay device. Examples of analytes include proteins, (e.g., proteins expressed by or caused to be expressed by *Plasmodium* infection, e.g., HRP II and III, aldolase, poly-asparagine proteins, lactate dehydrogenase, and fragments and variants thereof. Sandwich assays, for example, may be performed for analytes such as HRP II and III, aldolase, anti-asparagine proteins, lactate dehydrogenase and fragments and variants thereof. Competition assays, for example, may be carried out for analytes such as HRP II and III, aldolase, proteins with poly-asparagines, lactate dehydrogenase fragments and variants thereof.

It may be desired to assay two or more different analytes using the same device. In such instances, it may be desirable to employ different detectable markers on the same test strip where each detectable marker detects a different analyte. For example, different detectable markers may be attached to different mobile labeling reagents. The different detectable markers may be different fluorescent agents, which fluoresce at different wavelengths or differently colored dyes or particles. When detecting two or more different analytes using the same device, separate test detection or capture zones may optionally be formed on the test strip for each analyte to be detected. The same detectable marker may be used for all of the analytes. Alternatively, different detectable markers, as described above, may be used for the different analytes to prevent one capture zone being confused with another. For example, it is desirable to test for the presence of HRP II and/or HRP III and aldolase; HRP II and/or HRP III and poly-asparagine proteins; aldolase and poly-asparagine proteins; HRP II and/or HRP III, aldolase, and polyasparagine proteins and/or; HRP II and aldolase; HRP II and poly-asparagine proteins; HRP II, aldolase, and poly-asparagine proteins.

As used herein, a subject, is any animal, preferably a mammal. Mammals include, for example, sheep, goats, cows, pigs, horses, humans, and primates. A subject may be susceptible to malaria, e.g., living or visiting a high-risk area. Subject may be identified, selected, and/or diagnosed with malaria by self diagnosis or by a heath care professional.

As used herein, poly-asparagine proteins refer to proteins expressed by *Plasmodium* species that have from between about 5 to about 30; 6 and 25; 10 and 20; or greater than 12 or more than 6 consecutive asparagines in a row. For example, *P. falciparum* has 1473 annotated proteins with 6 asparagines in a row, 1107 proteins with 8 in a row, 733 proteins with 10 in a row, 456 proteins with 12 in a row, 334 proteins with 14 in a row, 246 proteins with 16 in a row, 184 proteins with 18 in a row, 135, proteins with 20 in a row, 114 proteins with 22 in a row. Exemplary poly-asparagine proteins include, for example, the proteins listed in Table 1 obtained from the sequenced genome. *P. falciparum* has multiple repetitive amino acid stretches within its annotated proteins. Notably polyasparagine is not cleaved by any known proteases and, for example, a 12-15 amino acid stretch of poly-asparagines survive intact in urine. As, approximately six amino acid define an immunoglobin epitope, antibodies to polyasparagine detect many *P. falciparum* poly-asparagine proteins or fragments thereof. Poly asparagine proteins were sequenced in Gardner, M J, et al. (2002). Genome sequence of the human malaria parasite *Plasmodium falciparum*. Nature 419:498-51 and referenced in Kissinger, J. C., et. al. 2002, "The *Plasmodium* Genome Database" Nature 419: 490-492 and they include 456 genes in *P. falciparum* and 6 genes in *P. vivax* and 4 genes in *P. knowlesi*, which is incorporated herein by reference in its entirety. Table 1:

TABLE 1

*P. FALCIPARUM* GENES WITH 12 OR MORE CONSECUTIVE ASPARAGINES

MAL13P1.122, MAL13P1.133, MAL13P1.158, MAL13P1.178, MAL13P1.184,
MAL13P1.203, MAL13P1.210, MAL13P1.222, MAL13P1.234, MAL13P1.243,
MAL13P1.258, MAL13P1.260, MAL13P1.266, MAL13P1.275, MAL13P1.278,
MAL13P1.286, MAL13P1.293, MAL13P1.296, MAL13P1.304, MAL13P1.323,
MAL13P1.333, MAL13P1.336, MAL13P1.38, MAL13P1.380, MAL13P1.39,
MAL13P1.405, MAL13P1.44, MAL13P1.63, MAL13P1.70, MAL13P1.93,
MAL7P1.102, MAL7P1.109, MAL7P1.115, MAL7P1.12, MAL7P1.120,
MAL7P1.127, MAL7P1.132, MAL7P1.137, MAL7P1.146, MAL7P1.147,
MAL7P1.15, MAL7P1.16, MAL7P1.164, MAL7P1.167, MAL7P1.17, MAL7P1.18,
MAL7P1.204, MAL8P1.104, MAL8P1.11, MAL8P1.113, MAL8P1.12, MAL8P1.139,
MAL8P1.153, MAL8P1.156, MAL8P1.19, MAL8P1.23, MAL8P1.24, MAL8P1.34,
MAL8P1.65, MAL8P1.7, MAL8P1.82, MAL8P1.92, PF07_0018, PF07_0022,
PF07_0024, PF07_0026, PF07_0028, PF07_0037, PF07_0038, PF07_0042,
PF07_0053, PF07_0056, PF07_0061, PF07_0086, PF07_0101, PF07_0116,
PF07_0118, PF07_0120, PF07_0126, PF08_0012, PF08_0016, PF08_0020,
PF08_0023, PF08_0026, PF08_0028, PF08_0030, PF08_0034, PF08_0040,
PF08_0060, PF08_0068, PF08_0096, PF08_0102, PF08_0111, PF08_0122,
PF08_0133, PF10_0031, PF10_0044, PF10_0045, PF10_0046, PF10_0057,
PF10_0075, PF10_0076, PF10_0078, PF10_0079, PF10_0083, PF10_0115,
PF10_0143, PF10_0150, PF10_0175, PF10_0179, PF10_0183, PF10_0197,
PF10_0209, PF10_0211, PF10_0213, PF10_0214, PF10_0234, PF10_0265,
PF10_0279, PF10_0292, PF10_0296, PF10_0307, PF10_0308, PF10_0320,
PF10_0322, PF10_0357, PF10_0361, PF11_0049, PF11_0064, PF11_0076,
PF11_0077, PF11_0086, PF11_0089, PF11_0091, PF11_0092, PF11_0101,
PF11_0111, PF11_0112, PF11_0127, PF11_0177, PF11_0201, PF11_0207,
PF11_0214, PF11_0218, PF11_0240, PF11_0241, PF11_0246, PF11_0276,
PF11_0317, PF11_0319, PF11_0324, PF11_0326, PF11_0329, PF11_0341,
PF11_0348, PF11_0357, PF11_0371, PF11_0375, PF11_0392, PF11_0395,
PF11_0396, PF11_0404, PF11_0418, PF11_0456, PF11_0464, PF11_0468,
PF11_0477, PF11_0479, PF11_0480, PF11_0528, PF13_0018, PF13_0035,
PF13_0048, PF13_0050, PF13_0078, PF13_0080, PF13_0097, PF13_0106,
PF13_0139, PF13_0148, PF13_0153, PF13_0155, PF13_0162, PF13_0163,
PF13_0167, PF13_0182, PF13_0187, PF13_0219, PF13_0225, PF13_0235,
PF13_0237, PF13_0257, PF13_0267, PF13_0321, PF13_0335, PF13_0339,
PF13_0350, PF14_0025, PF14_0031, PF14_0052, PF14_0059, PF14_0063,
PF14_0079, PF14_0084, PF14_0101, PF14_0108, PF14_0112, PF14_0114,
PF14_0123, PF14_0139, PF14_0143, PF14_0170, PF14_0172, PF14_0173,
PF14_0175, PF14_0179, PF14_0184, PF14_0186, PF14_0188, PF14_0195,
PF14_0197, PF14_0199, PF14_0228, PF14_0247, PF14_0250, PF14_0252,
PF14_0264, PF14_0266, PF14_0277, PF14_0282, PF14_0291, PF14_0293,
PF14_0300, PF14_0304, PF14_0315, PF14_0319, PF14_0327, PF14_0342,
PF14_0350, PF14_0374, PF14_0412, PF14_0442, PF14_0461, PF14_0463,
PF14_0471, PF14_0489, PF14_0494, PF14_0501, PF14_0507, PF14_0515,
PF14_0533, PF14_0550, PF14_0558, PF14_0561, PF14_0577, PF14_0594,
PF14_0613, PF14_0626, PF14_0649, PF14_0663, PF14_0710, PF14_0711,
PF14_0712, PF14_0722, PFA0120 c, PFA0140 c, PFA0165 c, PFA0180w,
PFA0215w, PFA0280w, PFA0320w, PFA0410w, PFB0265 c, PFB0280w, PFB0380 c,
PFB0460 c, PFB0510w, PFB0540w, PFB0705w, PFB0760w, PFB0800 c,
PFB0870w, PF C, 0085 c, PF C, 0235w, PF C, 0245 c, PF C, 0320w, PF C, 0335 c, PF C,
0380w, PF C, 0405 c, PF C, 0425w, PF C, 0440 c, PF C, 0485w, PF C, 0590 c, PF C,
0610 c, PF C, 0750w, PF C, 0760 c, PF C, 0770 c, PF C, 0820w, PF C, 0860w, PF C,
0960 c, PF C, 0965w, PFD0160w, PFD0170 c, PFD0185 c, PFD0200 c,
PFD0225w, PFD0285 c, PFD0375w, PFD0385 c, PFD0385w, PFD0535w,
PFD0545w, PFD0565 c, PFD0590 c, PFD0710w, PFD0835 c, PFD0840w, PFD0875 c,

TABLE 1-continued

PFD0885 c, PFD0940w, PFD0985w, PFD1045 c, PFD1100 c, PFD1105w,
PFD1115 c, PFD1135 c, PFE0120 c, PFE0130 c, PFE0320w, PFE0430w, PFE0440w,
PFE0465 c, PFE0485w, PFE0500 c, PFE0560 c, PFE0570w, PFE0655w, PFE0710w,
PFE0935 c, PFE1105 c, PFE1120w, PFE1145w, PFE1185w, PFE1260 c, PFE1325w,
PFE1390w, PFE1465w, PFE1555 c, PFF0095 c, PFF0125 c, PFF0195 c, PFF0220w,
PFF0295 c, PFF0380w, PFF0390w, PFF0445w, PFF0535 c, PFF0575 c, PFF0590 c,
PFF0620 c, PFF0655 c, PFF0670w, PFF0705 c, PFF0765 c, PFF0805 c, PFF0830w,
PFF0870w, PFF0910 c, PFF0985 c, PFF1065 c, PFF1145 c, PFF1225 c, PFF1260 c,
PFF1365 c, PFF1440w, PFF1460 c, PFF1470 c, PFF1475 c, PFF1485w, PFI0160w,
PFI0170w, PFI0185w, PFI0200 c, PFI0225w, PFI0260 c, PFI0285w, PFI0470w,
PFI0490 c, PFI0495w, PFI0550w, PFI0710 c, PFI0785 c, PFI0830 c, PFI0970 c,
PFI1015w, PFI1085w, PFI1120 c, PFI1155w, PFI1200w, PFI1265w, PFI1280 c,
PFI1300 c, PFI1335w, PFI1385 c, PFI1500w, PFI1510w, PFI1590 c, PFL0115w,
PFL0170w, PFL0275W, PFL0290w, PFL0350 c, PFL0360 c, PFL0425 c, PFL0545w,
PFL0555 c, PFL0600W, PFL0625 c, PFL0675 c, PFL0765c, PFL0855 c, PFL0930w,
PFL0975w, PFL1035w, PFL1075w, PFL1085w, PFL1125w, PFL1130 c, PFL1190 c,
PFL1310 c, PFL1335w, PFL1365w, PFL1375w, PFL1395 c, PFL1435 c, PFL1480w,
PFL1515 c, PFL1600 c, PFL1620w, PFL1635w, PFL1700 c, PFL1705w, PFL1735 c,
PFL1745 c, PFL1795 c, PFL1880w, PFL1900w, PFL1930w, PFL1935 c, PFL1990 c,
PFL2165w, PFL2240w, PFL2335w, PFL2390 c, PFL2490 c, PFL2520w

*P. VIVAX* GENES WITH 12 OR MORE CONSECUTIVE ASPARAGINES

Pv_3915-1-2260-2607; Pv_3915.phat_3 102573318; Pv_5054-6-521-270;
Pv_6571-2-545582-545830; Pv_6571.phat_95 102530884; Pv_6737-5-846809-838620;
Pv_6737.phat_910 102419958; Pv_6873-6-631938-631687; Pv_6875-3-136785-141518;
Pv_6875.phat_31 102294109

*P. KNOWLESI* GENES WITH 12 OR MORE CONSECUTIVE ASPARAGINES

Pk_1303g03p1 c, -2-2-349; Pk_235 c, 07p1 c, -1-1681-1845; Pk_253g04q1 c, -6-1862-1107;
Pk_313d05q1 c, -1-6853-7254; Pk_47b04q1 c, -2-524-679

Further proteins that may be detected, either alone or in combination in the methods and devices of the invention, include, for example, HRP II, which has gene sequence numbers chr7.phat_42 and chr7.phat_43 94% identity to 95% of P05227; Histidine-rich protein precursor (Clone PFHRP-II) in plasmo.db.; (HRP III has idenitification MAL13P1.480 histidine-rich protein III Other genbank numbers for HRP II and III include for example, U69552 HRP III from ITG2 from South America Sullivan MBP; U69551 HRP II from ITG2; X03144 from Stahl NAR 13:7837 1985 HRP III from FC27 that gave rise to D10; M15317 from, Irving & Cross Mol. Biochem. Parasitol. 18 (2), 223-234 (1986) *P. lophurae* duck malaria; X01469 See also Nature 312:616 1984 Ravetch *P. lophurae* duck malaria; M13987 hrp III 7G8 clone Wellems Proc. Natl. Acad. Sci. U.S.A. 83 (16), 6065-6069 (1986); M13986 hrp II 7G8 clone Wellems Proc. Natl. Acad. Sci. U.S.A. 83 (16), 6065-6069 (1986); K03509 with HRP II PNAS join; AF202093 HRP III FCC1/HN china Zhongguo Jishengchongbing Fangzhi Zazhi 14 (2), 95-99 (2001); AF142344 HRP II from FCC1/HN china; AF314756. 5'UTR of HRP III from Wellems group 7G8 clone; EST tags from Sibley 3D7; BU497960 hrp III 3D7; BQ739562 hrp III 3D7; BM275665 gametocyte 3D7 cDNA hrp II); AU088387 hrp ii 3d7 Sugano, S. Gene 200 (1-2), 149-156 (1997); AU088284 hrp ii 3D7 ibid; AU088247 hrp ii 3D7 ibid; AU087127 hrp ii 3D7 ibid. Also include GenBank accession numbers for HRP II AY816237-AY816310 and GenBank accession numbers for HRP III AY821805-AY821825. The gene for aldolase and lactate dehydrogenase are PF14_0425 fructose-bisphosphate aldolase; and PF13_0141 L-lactate dehydrogenase. Additional high abundance glycolytic genes which may appear in bodily fluids and useful in the methods and devices of the invention include, for example, CHR 13/PF13_0144 oxidoreductase, putative; CHR 10/PF10_0155 enolase; CHR 6/PFF1155w hexokinase; PF14_0341 glucose-6-phosphate isomerase; CHR 11/PF11_0294 ATP-dependent phosphofructokinase, putative; CHR 9/PFI0755c 6-phosphofructokinase, putative; CHR 3/PFC0831w triosephophate isomerase, putative; CHR 14/PF140378 triose-phosphate isomerase; CHR 14/PF140598 glyceraldehyde-3-phosphate dehydrogenase; CHR 9/PFI1105w Phosphoglycerate kinase; CHR 4/PFD0660w phosphoglycerate mutase, putative; CHR 11/PF11_0208 phosphoglycerate mutase, putative; CHR 6/PFF1300w pyruvate kinase, putative; CHR 6/PFF0895w malate dehydrogenase, putative; CHR 9/PFI1340w fumarate hydratase, putative; and CHR 10/PF10_0334 flavoprotein subunit of succinate dehydrogenase.

The term "sample" as used herein refers to any biological sample that could contain an analyte for detection. Preferably the biological sample is in liquid form or can be changed into a liquid form. Preferably, the sample is a urine sample or blood. Samples may also include, for example, serum, nasal discharge, urine, sweat, plasma, semen, cerebrospinal fluid, tears, pus, amniotic fluid, saliva, lung aspirate, gastrointestinal contents, vaginal discharge, urethral discharge, chorionic villi specimens, skin epithelials, genitalia epithelials, gum epithelials, throat epithelials, hair, and sputum. Samples may be buffered or may have their pH altered prior to being applied to the devices or being subjected to the methods of the invention. For example, a urine sample may be buffered with a buffer (e.g., Tris buffer, acid, base, etc) to a pH of between about 4.5 to about 9; to a pH of between about 5 to about 8.9; to a pH of about 7.5 to about 8.5, or a to a pH of about 6, 6.6, 7, 7.5, 7.6, 7.7, 7.8, 7.9, 8, 8.1, 8.2, 8.3, 8.4, 8.5, or 9. About, as used in the context of pH or other measurement or parameter described herein refers to the intrinsic variability due to reagents, apparatus, and human error in any measurement or apparatus or human interpretation of a parameter or result.

Sample volumes can range from between about 0.05 mL to about 20 mL, 0.1 to about 5; 0.1 to about 2; 0.1 to about 1 or 0.1 to about 0.5 mL of sample applied to the assay device. Alternately, enough sample should be applied to the assay device to ensure proper sample flow through the device, and to ensure proper flow of analyte (if present) through the device. Enough sample to ensure the mobility of the mobile labeling reagent is preferable. The amount of sample may depend, in part, on the absorbency of the sample receiving membrane, the absorbent sink, the length of the membranes, and width of the membranes, or the temperature of the device at the time of use and whether or not a reagent is added to the sample prior to the application of the sample to the sample receiving member.

The sample receiving membrane and the analyte detection membrane may be made of any substance having sufficient porosity to allow capillary action of fluid along its surface and/or through its interior. The porous material of either the sample receiving membrane or the analyte detection membrane should have sufficient porosity to allow movement of antibody- or antigen-coated particles. The porous material of either the sample receiving membrane or the analyte detection membrane should also be wettable by the fluid used in the sample, which contains the analyte to be detected e.g., HRP II and/or III, aldolase, and/or poly-asparagine proteins. Hydrophobicity of a porous material, sometimes referred to herein as a membrane, can be altered to render the membrane hydrophilic for use with aqueous fluid, by processes such as those described in U.S. Pat. No. 4,340,482, or U.S. Pat. No. 4,618,533. Examples of substances which can be used to form a porous material of either the sample receiving membrane or the analyte detection membrane include cellulose, nitrocellulose, cellulose acetate, glass fiber, nylon, polyelectrolyte ion exchange membrane, acrylic copolymer/nylon, and polyethersulfone. In a preferred embodiment, the porous material of either or both the sample receiving membrane and/or the analyte detection membrane are made of nitrocellulose. One skilled in the art will be aware of other porous materials that allow lateral flow.

The term "lateral flow" refers to liquid flow in which all of the dissolved of dispersed components of the liquid are carried, preferably, at substantially equal rates and with relatively unimpaired flow laterally through the material, as opposed to preferential retention of one or more components. Nitrocellulose has the advantage that proteinaceous reagents, such as an antibody, in the capture situs can be immobilized firmly without prior chemical treatment. If the membrane comprises paper, for example, the immobilization of an antibody in the second zone may be performed by chemical coupling using, for example, CNBr, carbonyldiimidazole, Sodium Periodate, or tresyl chloride.

Preferably the nitrocellulose sheet has a pore size of at least about 1 micron, even more preferably of greater than about 5 microns, and yet more preferably about 8-12 microns. Very suitable nitrocellulose sheet having a nominal pore size of up to approximately 12 microns, is available commercially from Sartorius GmbH (Goettingen, Germany).

Optionally, the nitrocellulose or other sample flow sheets may be "backed," e.g., with plastics sheet, to increase its handling strength. This can be manufactured easily by forming a thin layer of nitrocellulose on a sheet of backing material. The actual pore size of the nitrocellulose when backed in this manner will tend to be lower than that of the corresponding unbacked material. Alternatively, a preformed sheet of nitrocellulose can be tightly sandwiched between two supporting sheets of solid material, e.g., plastic sheets.

The term "mobile" as referred to herein means diffusively or non-diffusively attached, or impregnated.

Preferably the membranes are in the form of a strip or sheet to which during manufacture of the device, one or more reagents can be applied in spatially distinct zones. During use, the liquid sample is allowed to permeate through the sheet or strip from one side or end to another. Reagents that may be applied to the membranes of the invention include a capture reagent, a control reagent, and a mobile labeling reagent. The reagents may be diffusively or non-diffusively bound to the membranes.

If desired, a device according to the invention can incorporate two or more discrete bodies of membrane, e.g., separate strips or sheets, some carrying mobile and/or immobilized reagents. These discrete bodies can be arranged in parallel, for example, such that a single application of liquid sample to the device initiates sample flow in the discrete bodies simultaneously. The separate analytical results that can be determined in this way can be used as control results, or if different reagents are used on the different carriers, the simultaneous determination of a plurality of analytes in a single sample can be made. Alternatively, multiple samples can be applied individually to an array of carriers and/or analyzed simultaneously.

Following the application of a reagent to the capture situs, the remainder of the membrane may then be treated to block any remaining binding sites elsewhere. Blocking can be achieved by treatment with protein (e.g., bovine serum albumin or milk protein), or with polyvinylalcohol or ethanolamine, or any combination of these agents, for example. Between these process steps the membrane may be dried.

It is preferable that the flow rate of an aqueous sample through the membrane be such that in the untreated material, aqueous liquid migrates at a rate of about 1 to about 3 and preferably about 1.8 cm in approximately 1 minute, but slower or faster flow rates can be used if desired.

The spatial separation between the sample application membrane and the capture situs, and the flow rate characteristics of the membrane, can be selected to allow adequate reaction times during which the necessary specific binding can occur. Further control over these parameters can be achieved by the incorporation of viscosity modifiers (e.g., sugars and modified celluloses) in the sample to slow down the reagent migration.

Reagents can be applied to the membrane materials in a variety of ways. Various "printing" techniques are suitable for application of liquid reagents to the membranes, e.g., micro-syringes, pens using metered pumps, direct printing, ink-jet printing, air-brush, and contact (or filament) methods, and any of these techniques can be used in the present context. To facilitate manufacture, the membrane can be treated with the reagents and then subdivided into smaller portions (e.g., small narrow strips each embodying the required reagent-containing zones) to provide a plurality of identical carrier units.

As used herein, the term "sample receiving membrane," "sample receiving zone, and sample receiving region" are used interchangeably and refer to the portion of the assay device that may be in direct contact with the liquid sample, e.g., it receives the sample to be tested for the analyte in question. The sample can then migrate, for example, by lateral flow from the sample receiving membrane towards the capture situs and optionally to the absorbent sink. Preferably the sample receiving membrane is near one edge of the assay device. The sample receiving membrane is in flow contact with either a labeling reagent membrane or the analyte detection membrane. This could be an overlap, end-to-end connection, stacked or the like. The sample receiving membrane may be impregnated with buffer to neutralize reagents in the sample during the lateral flow immunoassay. The analyte in the sample should be capable of migrating, through lateral flow, with the liquid sample.

The sample receiving membrane can be made from any bibulous, porous or fibrous material capable of absorbing liquid rapidly. The porosity of the material can be unidirectional (e.g., with pores or fibers running wholly or predominantly parallel to an axis of the membrane) or multidirectional (omnidirectional, so that the membrane has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. It can be advantageous to pre-treat the membrane with a surface-active agent during manufacture, as this can reduce any inherent hydrophobicity in the membrane and therefore enhance its ability to take up and deliver a moist sample rapidly and efficiently. The sample receiving membranes can also be made from paper or other cellulosic materials, such as nitro-cellulose. Materials that are now used in the nibs of so-called fiber tipped pens are particularly suitable and such materials can be shaped or extruded in a variety of lengths and cross-sections appropriate in the context of the invention. Preferably the material comprising the porous receiving membrane should be chosen such that the membrane can be saturated with aqueous liquid within a matter of seconds. Preferably the material remains robust when moist. The liquid must thereafter permeate freely from the sample receiving membrane into the analyte detection membrane. Suitable materials also include cotton, cellulose, mixed fibers, glass fiber and the like. For example, paper such as 470 and 740-E from Schleicher and Schuell, Keen, N.H., or D28 from Whatman, Fairfield, N.J., can be selected for its high fluid absorption and wicking speed. A more porous material such as glass fiber #66078 from Gelman Sciences, Ann Arbor, Mich., or "POREX" from Porex Technologies, Fairburn, Ga., is suitable for impregnating labeled particles.

The absorption capacity of the sample receiving membrane may be sufficiently large to absorb the fluids that are delivered to the test strip or membrane. The sample-receiving zone serves to begin the flow of analyte-containing sample, and typically will be constructed of a material that exhibits low analyte retention. The sample-receiving zone may also function as a mechanical immobilization zone, entrapping any undesirable particulates present in the sample.

Devices of the invention may have an absorbent sink in flow contact with at least the analyte detection membrane. The absorbent sink may be formed of any absorbent substance. Examples of substances that may be used include cellulose, cellulose nitrate, cellulose acetate, glass fiber, nylon, polyelectrolyte ion exchange membrane, acrylic copolymer/nylon, Whatman 3MM, polyethersulfone, 470 and 740-E from Schleicher and Schuell, Keen, N.H., or D28 from Whatman, Fairfield, N.J., can be selected for their high fluid absorption and wicking speed.

The sample receiving membrane, the absorbent sink, the conjugate forming membrane all have a bottom or back surface. The bottom surface may have an adhesive applied to it so that it may be backed by a semi-rigid material to add strength to the membrane.

The absorbent sink may be made of the same material as the sample receiving membrane or it may be made of a different material. The sink, the sample receiving membrane and the analyte detection membrane may be made of the same material, or they may each be made of different materials.

"Labeling reagent," as used herein refers to a detectable marker, for example, a colored particle. Examples of particles that may be used include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; carbon black particles, colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads.

One preferred class of particles is colloidal gold particles. Colloidal gold particles may be made by any conventional method, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

Another preferred class of particles, are carbon particles, for example carbon black particles. The carbon label may be attached by methods well known to those skilled in the art, including the methods described in U.S. Pat. Nos. 5,252,496 and 5,559,041 to Princeton Biomeditech Corporation (Monmouth, N.J.), and U.S. Pat. Nos. 5,529,901; 5,294,370; 5,348,891 and 5,641,689 to ATO.

The selection of particle size may be influenced by such factors as stability of bulk sol reagent and its conjugates, efficiency and completeness of release of particles from conjugate pad, speed and completeness of the reaction. Also, the fact that particle surface area may influence steric hindrance between bound moieties may be considered. Particle size may also be selected based on the porosity of the porous material of either the sample receiving membrane or the analyte detection membrane. The particles are preferably sufficiently small to diffuse along the membrane by capillary action of the conjugate buffer.

Metal sols and other types of colored particles useful as marker substances in immunoassay procedures are also known per se. See, for example, U.S. Pat. No. 4,313,734, Feb. 2, 1982, to Leuvering, the disclosure of which is incorporated herein by reference. For details and engineering principles involved in the synthesis of colored particle conjugates see Horisberger, Evaluation of Colloidal Gold as a Cytochromic Marker for Transmission and scanning Electron Microscopy, Biol. Cellulaire, 36, 253-258 (1979); Leuvering et al, Sol Particle Immunoassay, J. Immunoassay 1 (1), 77-91 (1980), and Frens, Controlled Nucleation for the Regulation of the Particle Size in Monodisperse Gold Suspensions, Nature, Physical Science, 241, pp. 20-22 (1973).

The number of labeling particles present in the porous material of either the sample receiving membrane and/or the analyte detection membrane or test strip may vary, depending on the size and composition of the particles, the composition of the test strip and porous material of either the sample receiving membrane or the analyte detection membrane, and the level of sensitivity of the assay. The number of particles typically ranges between about $1 \times 10^9$ and about $1 \times 10^{13}$ particles, although fewer than about $1 \times 10^9$ particles may be used. In a preferred embodiment, the number of particles is about $1 \times 10^{11}$ particles.

Particles may be labeled to facilitate detection. Examples of labels include, but are not limited to, luminescent labels; colorimetric labels, such as dyes; fluorescent labels; or chemical labels, such as electroactive agents (e.g., ferrocyanide); enzymes; radioactive labels; or radio frequency labels.

Indirect labels, such as enzymes, e.g., alkaline phosphatase and horseradish peroxidase, can be used but these usually require the addition of one or more developing reagents such as substrates before a visible signal can be detected. Such additional reagents can be incorporated in the membranes, such that they dissolve or disperse in the aqueous liquid sample. Alternatively, the developing reagents can be added to the sample before contact with the membranes or the membranes can be exposed to the developing reagents after the binding reaction has taken place. Coupling of the label to the mobile labeling reagent may be by covalent bonding, or by hydrophobic bonding. Such techniques are commonplace in the art. In a preferred embodiment, where the label is a direct label such as a colored latex particle, hydrophobic bonding is preferred.

The presence or intensity of the signal from the label which becomes bound in the capture situs can provide a qualitative or quantitative measurement of analyte in the sample. A plurality of detection or capture zones arranged in series on the membrane, through which the aqueous liquid sample can pass progressively, can also be used to provide a quantitative measurement of the analyte, or can be loaded individually with different specific binding agents to provide a multi-analyte test.

The reagents that are mobile or releasably bound are capable of dispersing with the liquid sample upon rehydration and are carried by the liquid sample in the lateral flow. The terms "immobile" or "immobilized" as used herein refer to reagents which are attached to the support such that lateral flow of the liquid sample does not affect the placement of the immobile particle in the discrete membrane of the porous material. Such attachment can be through covalent, ionic or hydrophobic means. Those skilled in the art will be aware of means of attachment to immobilize various particles.

The term "mobile labeling reagent" refers to a suitable reagent labeled with a particle described above. The mobile labeling reagent may be a protein or molecule which recognizes or binds to the analyte in question, and which is conjugated or attached to a substance or particle capable of producing a signal that is detectable by visual or instrumental means. The attachment to the substance or particle capable of producing a signal may be chemical, covalent or noncovalent, ionic or non-ionic. The particle or molecule recognizing the analyte can be either natural or non-natural, preferably monoclonal, polyclonal, or a fragment of an antibody or a lectin.

Mobile labeling reagents may be, for example, an antibody to HRP II, HRP aldolase, and/or poly-asparagine proteins or fragments or variants thereof. The poly-asparagine repeats of the poly-asparagine proteins are a repeated epitope in *Plasmodium* species. Thus, a sandwich complex can be formed even if the indicator capture reagent and the indicator labeling reagent each contain an antibody to the same epitope (e.g., poly-asparagines).

The term "labeling reagent membrane" refers to a membrane which contains indicator labeling reagent. The labeling reagent membrane may also contain control labeling reagent. The separate labeling reagent membrane is preferably made of a mixture of cellulose and polyester, or other porous material.

The term "discrete situs," "capture situs" or "control sifts" as used herein refer to a defined area in which either the mobile labeling reagents, the capture reagent, or the control reagent are impregnated or immobilized to the membrane.

The situs of the control capture reagent or the capture reagent for the analyte provide a discrete visible signal in a desired geometric shape from which to view the results of the test. For example, if the one mobile labeling reagent is analyte bound to anti-analyte conjugated to Blue latex label, then a discrete blue signal will appear at the discrete capture situs if the indicator capture reagent binds and immobilizes the analyte-labeling reagent complex. If the control labeling reagent is BSA conjugated to a label such as colored latex or gold sol, then a discrete signal will form at the discrete control sifts if the control capture reagent has immobilized the BSA-control labeling reagent.

Control reagents according to the invention may be used to perform a variety of control functions. For example, control reagents may be used to ensure that the assay device is in good working order, they may be used to determine whether the sample has wicked through the membranes properly, they may function to indicate when the assay may be read, e.g., signal the end of the reaction, they may function as internal standards and allow analyte measurement results to be compared between different test strips, and can be useful in demonstrating that the indicator labeling reagent is intact which can provide an indication of the ongoing functionality of the indicator labeling reagent.

A wide variety of reagents are known in the art that may be used as a control reagent. For example, a naturally occurring or engineered protein may be used to bind unbound mobile labeling reagent. The control reagent may also be one member of a pair of a receptor-ligand pair. Additionally, at least one membrane of the control reagent may be an antigen, another organic molecule, or a hapten conjugated to a protein non-specific for the analyte of interest. Descriptions of other suitable control reagents may be found in U.S. Pat. No. 5,096,837, and include IgG, goat anti-mouse antibodies, other immunoglobulins, bovine serum albumin (BSA), other albumins, casein, and globulin or portions thereof. As a further alternative, a control zone could contain immobilized analyte which will react with excess labeled reagent from the first zone. As one purpose of the control zone is to indicate to the user that the test has been completed, the control zone should be located downstream from the capture situs in which the desired test result is recorded. A positive control indicator therefore tells the user that the sample has permeated the required distance through the test device.

Desirable characteristics for control reagents include, but are not limited to, stability in bulk, non-specificity for analyte of interest, reproducibility and predictability of performance in test, molecular size, avidity of binding for each other, ability to bind to a membrane, binding availability upon biding to membrane, and immobilization potential.

The devices of the present invention also may include a procedural control which comprises visible moieties that do not contain the specific binding agent or analyte competitor and that are also carried through to a control area of the capture zone by the liquid flow. These visible moieties are coupled to a control reagent which binds to a specific capture partner and can then be captured in a separate procedural control portion of the capture zone to verify that the flow of liquid is as expected. The visible moieties used in the procedural control may be the same or different color than those used for the test moieties. If different colors are used, ease of reading the results is enhanced. In one preferred embodiment, the procedural control may include a signal that become visible when the sample wicks through the portion of the membrane in the location of the signal. The procedural control may be a line drawn on the housing beneath the membrane, it may be a line on the backing beneath the test strip, or it may be a reagent adhered to, in, on, or within the membrane that becomes visible upon contact with a sample. Alternatively, the control zone can contain an anhydrous reagent that, when moistened, produces a color change or color formation, e.g., anhydrous copper sulphate which will turn blue when moistened by an aqueous sample.

In a preferred embodiment, the membranes include more than one control zone or situs and may be used to create a calibration curve against which a wide variety of analyte measurement results may be compared. Having the test strip possess more than one control zone allows lateral flow assays to have a wider dynamic range than conventional lateral flow assays. In preferred embodiments, test strips with 2, 3 or more control zones are used with a relative scale methodology, discussed further below, that permits mapping of amounts of control binding pairs detected onto the same scale on which amounts of analyte detected are reported.

The devices of the invention may also, be used to determine quantitatively the amount of analyte in a sample. Once the amount of detectable markers has been measured in each test zone, these measurements may be used to detect and preferably quantify the amount of analyte present, preferably by also calibrating the test device using the amounts of detectable markers in one or more control zones.

Examples of detection techniques useful in the invention include seeing a visible signal with the eye and optical methods (light scattering, simple reflectance, luminometer or photomultiplier tube); radioactivity; electrical conductivity; dielectric capacitance; and/or electrochemical detection of released electroactive agents.

In certain preferred embodiments, the mobile labeling reagent and the immobile capture reagent are antibodies specific for the analyte. Preferably, the mobile labeling regent and the immobile capture reagent recognize and bind to, for example, different portions of the analyte or to different subunits of the analyte. Antibodies may be polyclonal or monoclonal or fractions thereof. Polyclonal antisera and indeed monoclonal antibodies or fractions thereof having specific binding properties and high affinity for virtually any antigenic substance are known and commercially available or can be produced from stable cell lines using well known cell fusion and screening techniques. The literature is replete with protein immobilization protocols. See, for example, "Laboratory Techniques in Biochemistry and Molecular Biology," Tijssen, Vol. 15, Practice and Theory of Enzyme immunoassays, chapter 13, The Immobilization of Immunoreactants on Solid Phases, pp. 297-328, and the references cited therein.

Examples of antibodies useful in the methods and device of the invention include the anti-HRP II, anti-HRP HI antibodies (e.g., 3A4), anti-aldolase antibodies (e.g., 2E12 or 6B10), anti-poly-asparagine protein antibodies (e.g., antibodies specific for one or more of proteins with poly-asparagines, e.g., specific to the poly asparagine motif.) For example, as is discussed below, the mobile labeling reagent recognizes a poly-asparagine protein or a fragment thereof, the capture reagent recognizes the anti-poly asparagine capture reagent (e.g., antibody or fragment thereof), and the control agent recognizes the unbound capture reagent.

As used herein, "capture situs," "detection situs," and "capture zone" are used interchangeably. The immobilized capture reagent is bound at the capture situs on the analyte detection membrane. The capture situs may be impregnated throughout the thickness of the membrane in the capture situs (e.g., throughout the thickness of the sheet or strip if the carrier is in this form). Such impregnation can enhance the extent to which the immobilized reagent can capture any analyte or labeled reagent, present in the migrating sample. Alternately, the immobilized capture reagent is bound only to one or both of the surfaces of the membrane or only impregnates partially the thickness of the membrane.

The results of an analysis conducted using a device according to the invention may be read in the capture zone by noting the presence or absence of a visible signal at the location of the capture situs or zone. For example, a labeling reagent bound to an analyte will bind to the capture zone and concentrate the label such that it is visible. The use of a control is helpful for indicating the time when test results can be read, as described above. Thus, when the expected signal appears at the control situs, the presence or absence of a color in the capture situs can be noted. The use of different colors for test and control regents or labels aids in this process.

Capture reagents may be applied to, for example, the analyte detection membrane via printing, spotting, and like techniques. One skilled in the art having the benefit of this disclosure, would know the appropriate technique for their intended purpose. Optionally, after the application of the capture reagent to the membrane, a blocking agent or agents may be applied or immobilized in situ.

The capture reagent is immobile, e.g., is not affected by the lateral flow of the liquid sample due to the immobilization to the porous material. The particle or molecule of the indicator capture reagent can be natural, or non-natural, e.g., synthetic. Once the indicator capture reagent binds the analyte-mobile labeling reagent(s) complex it prevents the analyte-mobile labeling reagent from continuing with the lateral flow of the liquid sample.

The terms "analyte detection membrane," "analyte detection region," and "analyte detection situs," as used herein, refer to the portion of the assay device which is in lateral flow contact with the absorbent sink, and either or both of the porous material of the sample receiving membrane and/or the porous material of the conjugate forming membrane or region. The contact between the membranes can be an overlap, stacked or end-to-end contact or any other configuration that allows flow contact. The analyte in the sample should be capable of migrating through the membranes with lateral flow, e.g., capillary flow, with the liquid sample. The analyte detection membrane may be made of a porous material. Preferably, the analyte detection membrane is made of nitrocellulose. The analyte detection membrane can contain the mobile labeling reagents, the immobile indicator capture reagent and the immobile control capture reagent. In other embodiments, the analyte detection membrane contains only the immobilized control capture reagent and the capture reagent. In certain embodiments, one or more of the analyte detection membrane, sample receiving membrane, mobile labeling reagent membrane, and absorbent sink are made of the same materials and may be made of a single piece of material that contains zones or regions.

Features of the analyte detection membrane include its ability to wick fluids and to bind proteins. Exemplary materials include nitrocellulose, nylon or the like. In a preferred embodiment of this invention, the material is nitrocellulose with or without laminated solid support such as polyester. Nitrocellulose is readily available from numerous suppliers, as discussed above.

The immobilized capture reagent in the capture situs is preferably a highly specific antibody, and more preferably a monoclonal antibody. In one embodiment of the invention involving a sandwich type reaction, the mobile labeling reagent is also preferably a highly specific antibody, and more preferably a monoclonal antibody.

The "conjugate forming membrane," "conjugate forming region," and "conjugate forming zone" are used interchangeably herein and may have releasably bound thereto an enzyme-antibody conjugate or particulate moieties which may or may not be visible, and which can be detected if accumulated in the capture zone. The visible moieties, as described above, can be dyes or dyed polymers which are visible when present in sufficient quantity, or can be, and are preferred to be particles such as dyed latex beads, liposomes, or metallic, organic, inorganic or dye solutions, for example, carbon black, dyed or colored cells or organisms, red blood cells and the like. The enzyme-antibody conjugate or particulate moieties used in the assay provide the means for detection of the nature of and quantity of result, and accordingly, their localization in the capture situs or zone may be and is preferably a function of the analyte in the sample. In general, this can be accomplished by coupling the enzyme-antibody conjugate or particulate moieties to a ligand that binds specifically to the analyte, or which competes with analyte for a capture reagent in the capture zone.

In one approach, the conjugate, or particulate moieties are coupled to a specific binding partner that binds the analyte specifically to form, for example a mobile labeling reagent. For example, if the analyte is an antigen, a labeled antibody specific for this antigen may be used or a labeled immunologically reactive fragments of the antibody, such as $Fab'_2$, Fab or Fab', or other fragment or binding member of an antibody, may also be used. These mobile labeling reagents may then bind to an analyte in a sample as the sample passes through the labeling zone or situs and are carried into the capture situs by the liquid flow. When the complex reaches the capture zone or situs, it is captured by an analyte-specific capture reagent, such as an antibody. For example, the labeled antibody is an anti-HRP II and/or anti-HRP III antibody and the capture regent is an anti-antibody antibody. Excess liquid sample may be taken up by the absorbent sink.

In another approach, the conjugate or particulate moieties are coupled to a labeled ligand which is competitive with analyte for a capture reagent in the capture situs, most typically, other molecules of the analyte itself. Both the analyte from the sample and the labeled competitor bound to the conjugate or particulate moieties are then carried into the capture zone. Both analyte and its competitor then react with the capture reagent, which in this instance is also typically specifically reactive with an analyte and its competitor. The unlabeled analyte thus is able to reduce the quantity of competitor-conjugated conjugate or particulate moieties that are retained in the capture zone. This reduction in retention of the conjugate or particulate moieties becomes a measure of the analyte in the sample.

The term "adequate mechanical strength," as used herein, refers to a desired support to the assay device so as to function properly. The adequate mechanical strength is the support achieved for the entire assembled assay device so as to function properly in the collection and analysis of the analyte in the liquid sample. The total thickness of all of the layers of the immunoassay device is preferably at least 0.003 inches thick. The total thickness of the immunoassay device consists of the thickness of the backing, the membrane elements, label pads (if desired), and the cover. This minimum total thickness is desired in order to produce the desired adequate mechanical strength or support for the device to function effectively. Adequate mechanic strength, in the test strip embodiment, may be achieved, for example, by the backing.

The term "plastic material," or "plastic cover," "cover," or "housing" as used herein refers to any plastic material, which can cover the porous material of the device. Preferably, this is Mylar®, however, those skilled in the art will know of various materials that can be used for such purposes. For example, Mylar®, vinyl, other polyesters, polycarbonate, methyl methacrylate polymer, polystyrene, polyethylene, polypropylene, or waxed cardboard. The housing can be one continuous plastic or separate pieces as shown in the Figures. The housing allows the discrete control and discrete capture situses to be viewed and allows for sample to be applied to the sample application membrane. Thus, if the cover is clear then the result can be viewed through the clear cover. If the cover is opaque, then a window, aperture, gap or hole is present in the housing so the results can be viewed.

The structure of the test strip with a backing may be a laminate structure with the backing adhered to a back of the test strip to provide adequate mechanical strength to the device, e.g., to provide support and strength characteristics of the porous material and overall device such that lateral flow of liquid through the device will not be interrupted, for instance by the collapse or disintegration of the device upon wetting. Additional support for the device during the immunoassay may be provided by the walls of a test tube against which the device may rest during the lateral flow.

The term "top" refers to the upper surfaces of the membranes of the device, e.g., the top surface of the test strip.

Test strip backing according to the present invention may be made of, for example, mylar, vinyl, polyester, polycarbonate, methyl methacrylate polymer, polystyrene, polyethylene, polypropylene, and waxed cardboard.

Alternatively, the backing may be a molded plastic backing. The backing may have a thickness of between about 0.001 inches to about 0.010 inches. The backing material may have an adhesive on one side so as to attach the porous material or membrane. The structure of the test strip with a backing may be a laminate structure with the backing covering the back of the test strip and providing adequate mechanical strength to the device, e.g., providing support and strength characteristics of the porous material and overall device such that lateral flow of liquid through the device will not be interrupted, for instance by the collapse or disintegration of the device upon wetting.

A method of using the invention includes the steps of applying a sample to an assay device; and observing a result of the assay. The devices described above may be used in the methods.

The devices of the invention may also be packaged individually or with multiple devices. Each device may be used only one time or they may be designed for multiple uses. The devices may also be packaged as a kit with instruction sheets to inform the user on the proper use of the device.

Figure 14:
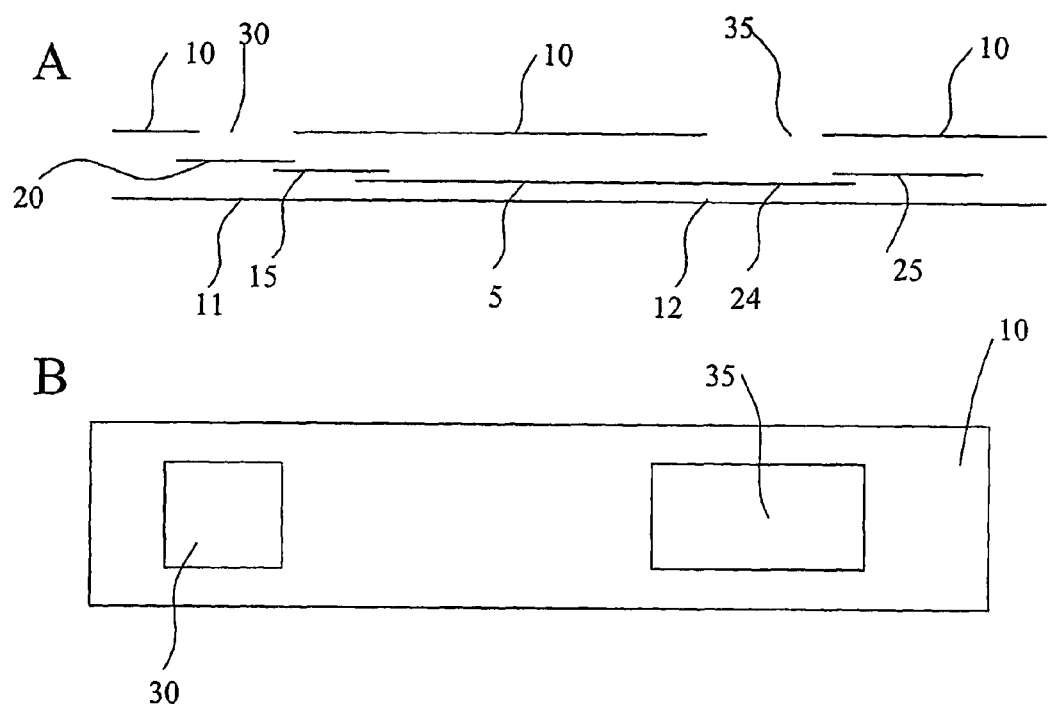
FIGS. 14A and B depict schematics of a device according to the invention.

FIG. 14A is a schematic view of one device according to the invention. The device incorporates a porous analyte detection membrane 5, running almost the length of housing 10 and 11. A procedural control 12 is located on a top surface of the interior of the housing 11. The analyte detection membrane 5 is in lateral flow contact with a conjugate forming membrane 15 and sample receiving membrane 20. The analyte capture situs 24 is also in lateral flow contact with the absorbent sink 25. The sample receiving membrane 20 is located beneath the sample application aperture 30 such that a sample applied through the sample application aperture 30 would be received by the sample receiving membrane 20. The sample would then flow through the conjugate forming membrane and mobilize the mobile labeling reagent contained in, on, releasably immobilized on, or adhered to the conjugate forming membrane. The housing 10 has, in addition to the sample application aperture 30, an observation window 35 positioned to allow a view of the capture situs, the control situs (240 and 246 of FIG. 15), and a procedural control 12.

FIG. 14B is a schematic of the top of the housing 10 of FIG. 14A. The top of the housing 10 has a sample application aperture 30 and an observation window 35. The observation window may be fitted with a transparent or semi-transparent material that is impervious or semi-impervious to water or it may be an aperture that is not fitted with any materials. Window materials for use in the invention, include, glass, polypropylene, and the like. A person skilled in the art would be able to determine proper window materials for a particular purpose having the benefit of this disclosure.

Figure 15:
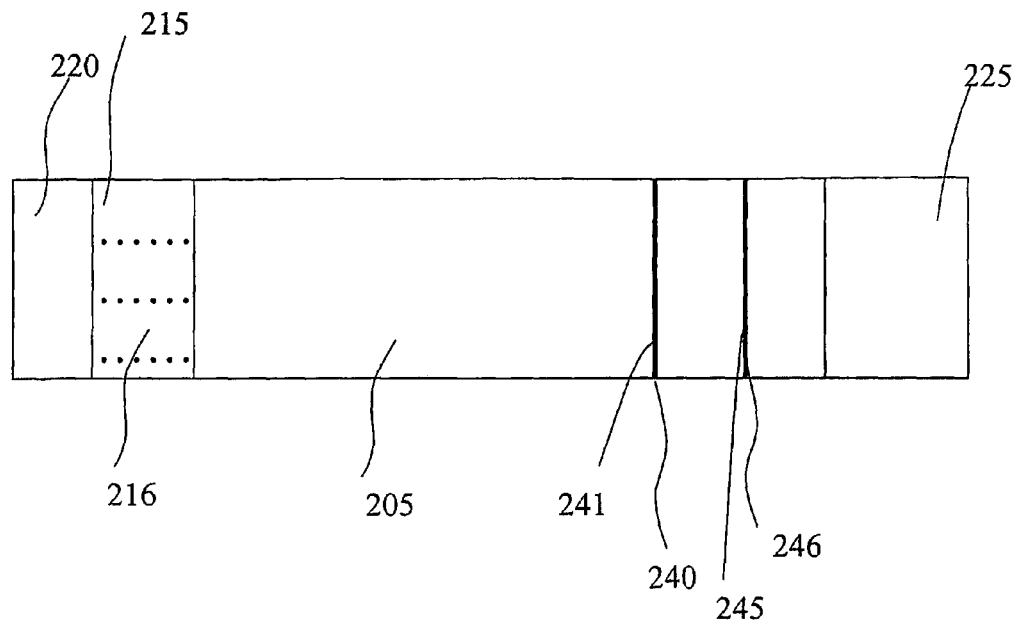
FIG. 15 depicts a top view of a device according to the invention.

Referring to FIG. 15, a top view of the lateral flow membranes according to one embodiment of the invention is shown. A sample receiving membrane 220 is in lateral flow contact with a conjugate forming membrane 215, an analyte detection membrane 205, and an absorbent sink 225. The conjugate forming membrane 215 has releasably bound to it a mobile labeling reagent 216 that will be mobilized when in contact with a fluid. The analyte detection membrane 205 has an immobilized capture reagent 240 at a capture situs 241 and a control reagent 245 at a control situs 246.

Figure 16:
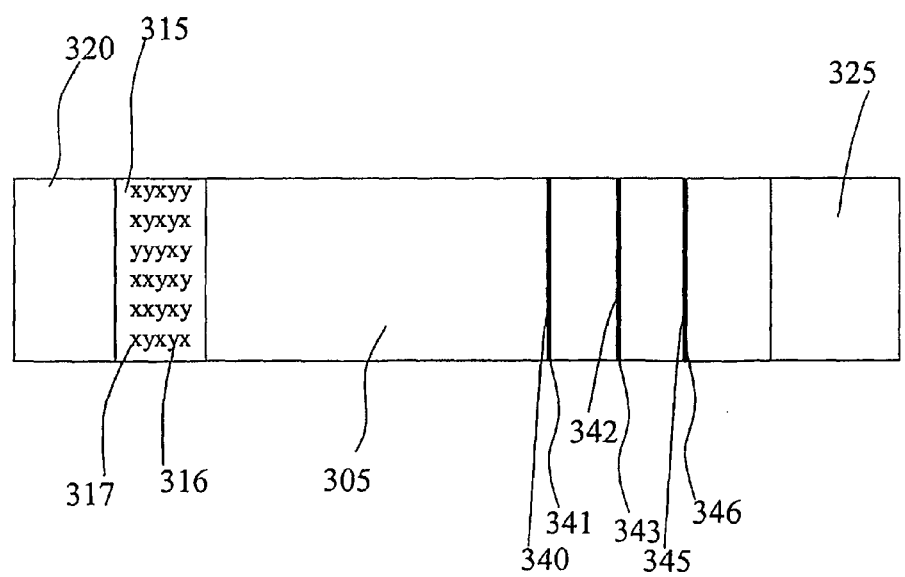
FIG. 16 depicts a top schematic view of a device according to the invention.

FIG. 16 illustrates another embodiment of the invention. A top view of the lateral flow membrane according to another embodiment of the invention is shown. A sample receiving membrane 320 is in lateral flow contact with a conjugate forming membrane 315, an analyte detection membrane 305, and an absorbent sink 325. The conjugate forming membrane 315 has releasably bound to it two mobile labeling reagents 316 and 317 that will be mobilized when in contact with a fluid. Each mobile labeling reagent is specific for a different analyte. The analyte detection membrane 305 has two immobilized capture reagents 340 and 342 at capture situs 341 and capture situs 343, respectively. The capture reagents are specific for one or the other of the mobile labeling reagents when bound to an analyte. There is also an immobilized control reagent 345 at a control situs 346 to serve as a control that the assay is functioning.

FIG. 17 depicts a further embodiment of the invention suitable for use as a dipstick wherein the sample to be analyzed is introduced to the lateral flow apparatus by dipping the device into the sample or by flowing the sample over the sample receiving zone of the device. Referring to FIG. 17, the test strip 455 has a grip zone 419 to allow handling of the test strip and a sample application zone 420, which is in lateral flow contact with the conjugate forming region 415 containing a labeled specific binding reagent 416. The sample receiving zone is also in flow contact with the absorbent sink 425. The absorbent sink is covered with a covering, for example a plastic film. The film covered absorbent sink may be a grip zone or may be in addition to grip zone 419 as shown. Distal to the conjugate forming region 415 is the capture situs 440 and the control situs 445. Immobilized on the test strip at the capture situs 440 is a capture reagent. The test strip is backed by backing 450 on the bottom surface 456 of the assay strip 455.

In operation, the sample application zone 420 may be exposed to an aqueous sample, e.g., by dipping the end of the test strip into a sample or by applying a sample to the end of the test strip with a sample applicator. The liquid sample will then permeate the length of test strip 455, for example, by capillary flow. The sample will mobilize the mobile labeling reagent 416 from the conjugate forming region 415 and can bind to an analyte if present in the sample. As the sample permeates the test strip it travels through the capture situs 440 and the control situs 445. At the capture situs, any analyte bound to mobile labeling reagent may bind to the capture reagent to be detected, for example, through a "sandwich" reaction involving an analyte in the sample. Any unbound mobile labeling reagent will pass through the capture situs and may be bound at the control situs 445 by the control reagent.

FIG. 18 in an alternate embodiment of a device according to the invention. A top view of the lateral flow membranes according to one embodiment of the invention is shown. A sample receiving membrane 520 is in lateral flow contact with a conjugate forming membrane 515, an analyte detection membrane 505, and an absorbent sink 525. The conjugate forming membrane 515 has releasably bound to it a mobile labeling reagent 516 that will be mobilized when in contact with a fluid. The analyte detection membrane 505 has an immobilized capture reagent 540 bound there to or located there on at a capture situs 541 and a control reagent 545 at a control situs 546.

Many circumstances may affect the absolute reactivity of lateral flow assays, including, but not limited to, manufacturing-derived variations, operator induced variations, environmentally induced variations and sample effects. With conventional lateral flow assays, any of these variations may act to repress or arguably enhance reactivity of one strip over another, resulting in possible false negative or false positive results. Not controlling for these or other variations may result in significant imprecision, non-reproducibility, lack of sensitivity and lack of specificity of the tests.

Such devices can be provided as kits suitable for home use, comprising a plurality (e.g., two) of devices individually wrapped in moisture impervious wrapping and packaged together with appropriate instructions to the user. The instructions, for example, may provide information on malaria diagnosis, interpretation of the test result and selection of subjects to receive the test.

Kits of dipstick embodiments may include a plurality of devices, for example, more than one device, e.g., 10, 25, 100, 150 or 1000 devices may be packaged together with instructions for use. Instructions for use may include testing procedures, interpretation procedures, performance characteristics, and information on the test device.

Kit of devices enclosed in housing according to the invention may be packaged with one or more devices, for example, 5, 10, 25, 30, 100 or 1000 or more devices may be packaged and sold together with instructions for use. Optional other materials provided in the kit may include an control set with negative, positive controls. The instructions may contain information on storage and handling of the devices after purchase and information in the testing procedures.

Kits may include, for example:

25 Test Sticks in a container;
25 Test Tubes;
25 Transfer Pipettes;
25 Capillary Tubes with 1 Capillary Bulb;
1 Diluent (contains buffer with 0.2% sodium azide);
1 Mono Positive Control (contains rabbit anti-beef stroma in tris buffer with 0.2% sodium azide; and
  0.05% gentamycin sulfate preservatives);
1 Mono Negative Control (contains goat albumin in tris buffer with 0.2% sodium azide);
1 Work Station; and
1 Directional Insert Other features and advantages of the invention will be apparent from the following detailed description of the presently preferred embodiments of the invention in conjunction with the accompanying drawings and from the claims.

EXAMPLES

It should be appreciated that the invention should not be construed to be limited to the examples, which are now described; rather, the invention should be construed to include any and all applications provided herein and all equivalent variations within the skill of the ordinary artisan.

Example 1

Figure 2:
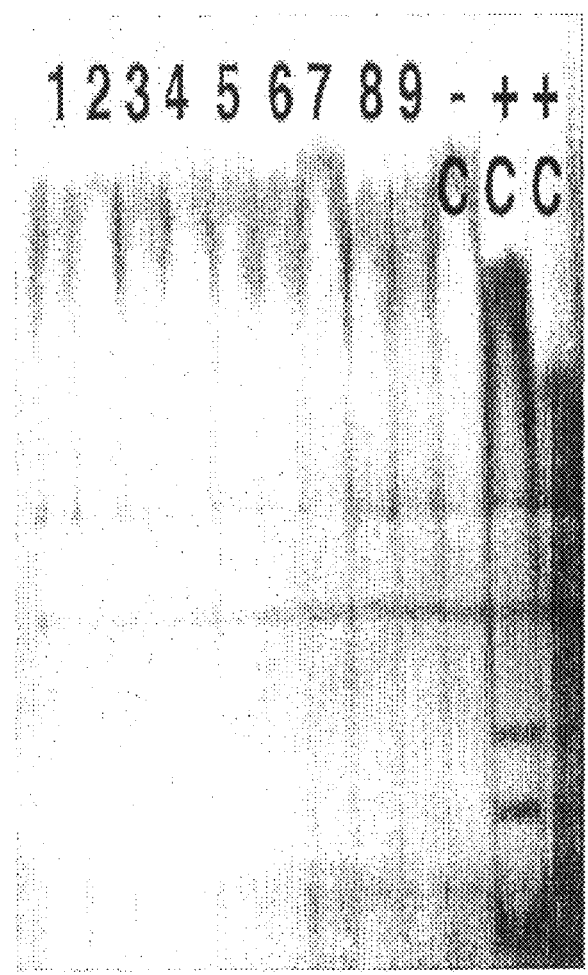
FIG. 2 shows lack of detection of intact lactate dehydrogenase by a blood based immunochromatographic test in the urine. 15 microliters of urine was mixed with reagents. No Pf LDH is detected in the nine urine samples corresponding to Mal urine 1-9 in FIG. 1 by this analysis. Without wishing to be bound by any scientific theory, this particular antibody may detect native noncleaved antigen only.
Figure 4:
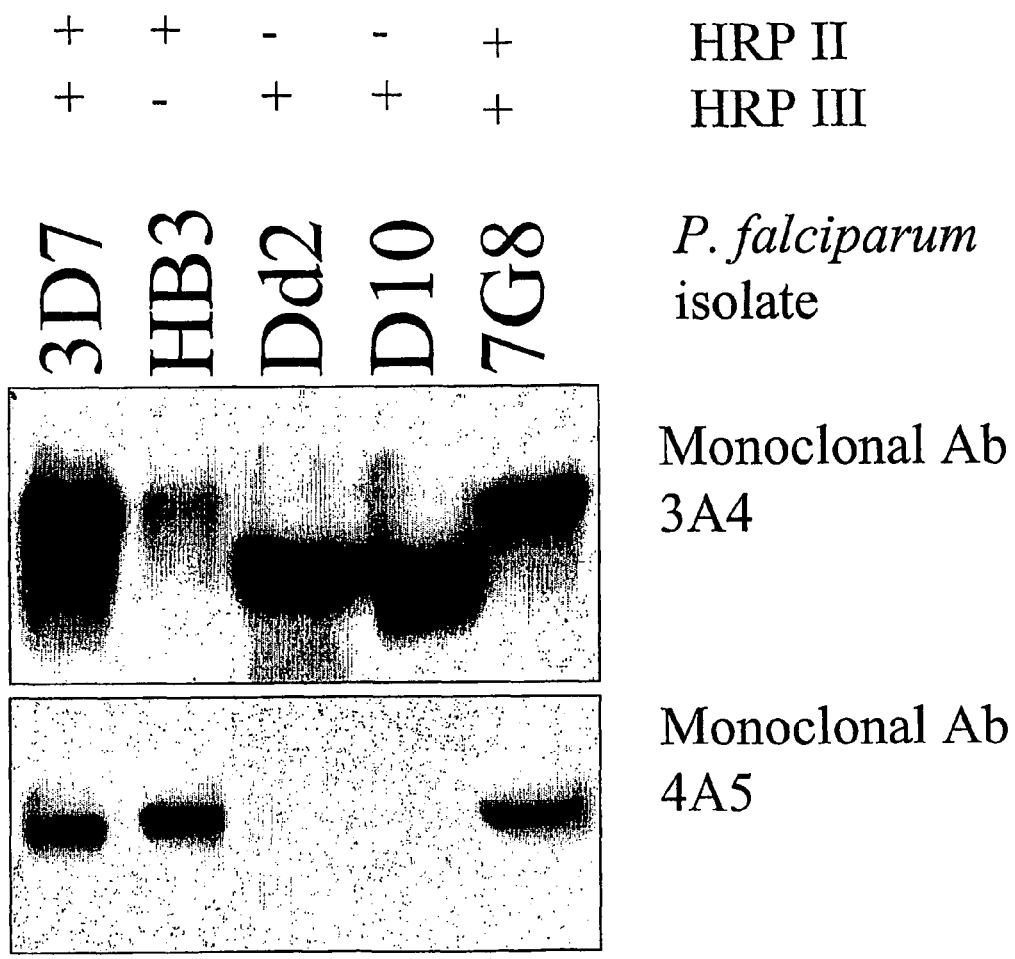
FIG. 4 depicts that monoclonal anti-HRP II and III antibodies detect HRP II and III from worldwide divergent isolates. HB3 has only HRP II, Dd2 and D10 have only HRP III and 3D7 and 7G8 have both HRP II and III. This suggests 3A4 antibody has a higher affinity for both HRP II and III while 4A5 does not detect HRP III as well.
Figure 5:
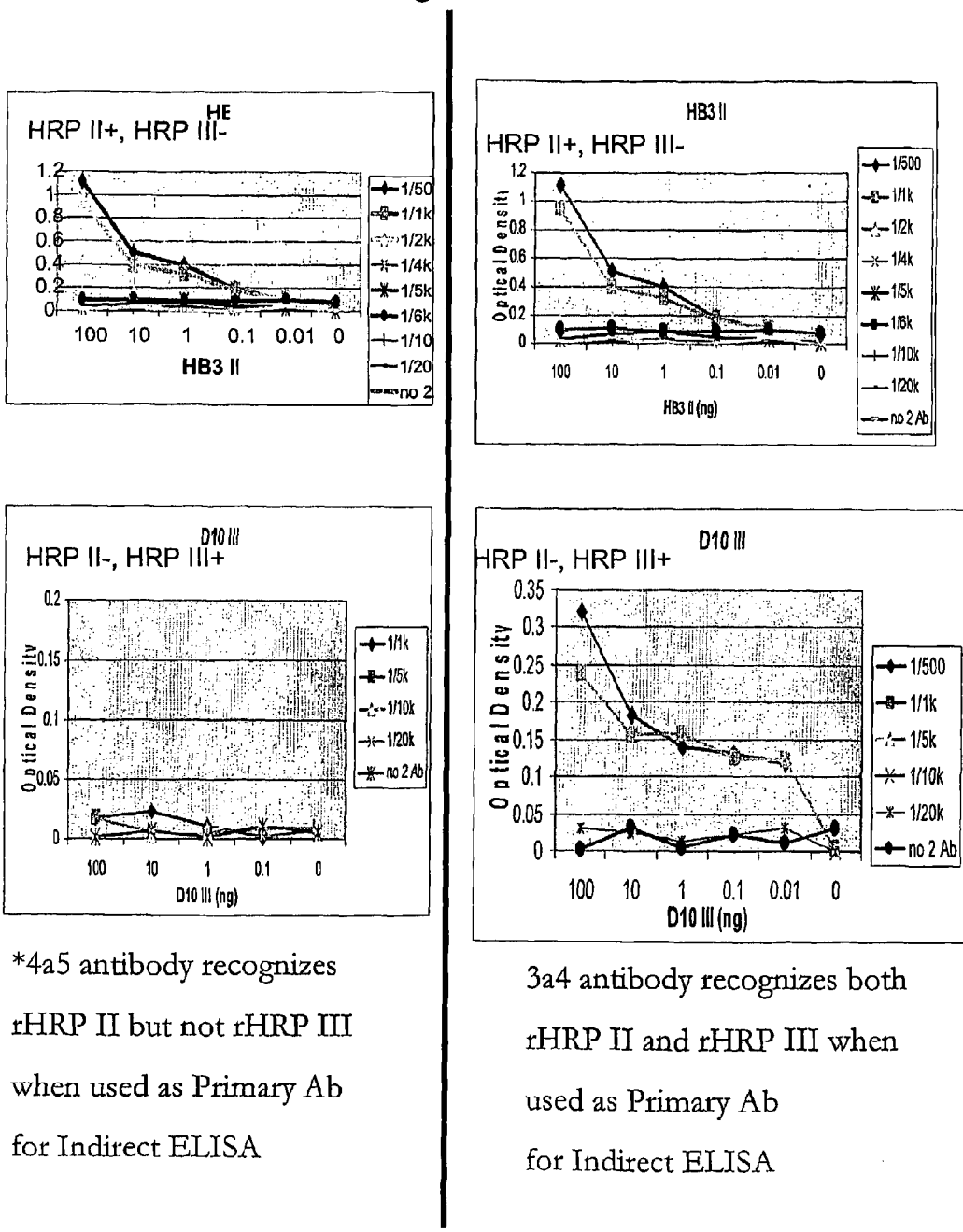
FIG. 5 depicts an anti-HRP II and III antibodies which are specific for HRP II on recombinant HB3-HRP II and recombinant D10 HRP III by ELISA.
Figure 6:
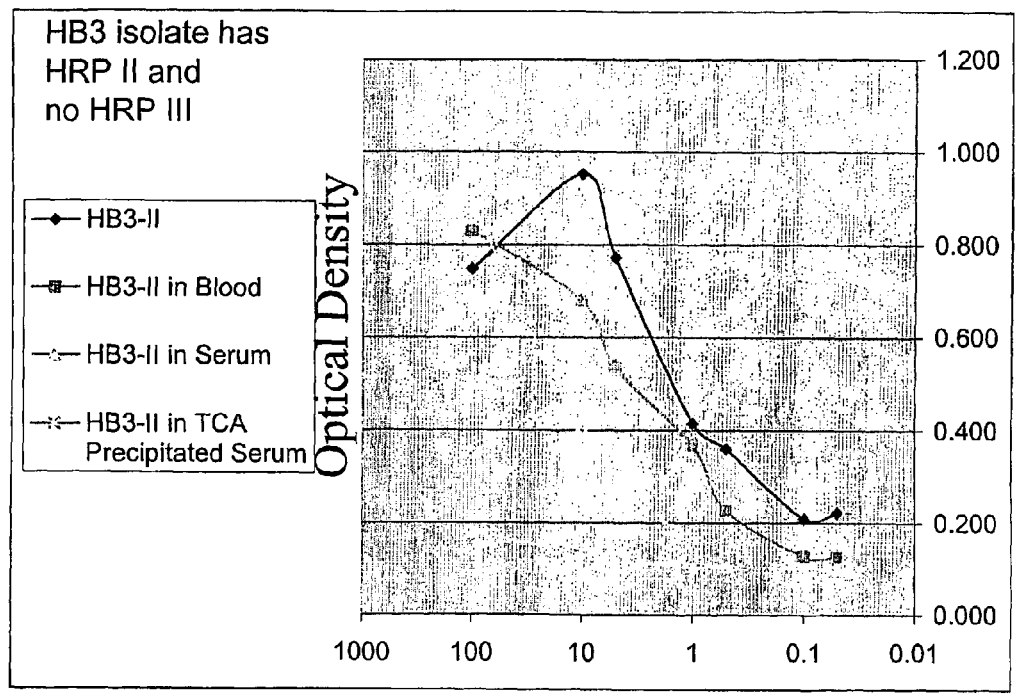
FIG. 6 depicts detection of recombinant HB3 HRP II in blood and serum. Lower limit of detection is approximately a nanogram of HRP II. A million parasites contain approximately 1.3 ng of PfHRP II. The approximate lower level of detection is 10,000 parasites per microliter (~0.1% parasitemia) for a direct dilution of 10 μl in 100 μl of assay.

Of the analyzed, frozen archival from 2001, 12 urine samples with blood films positive for malaria from Zambia, it was found that 10 of 12 (83%) were positive for PfHRP II and/or by the blood based Binax malaria Pf/Pv NOW®ICT. It was also found that 4 of 12 positive for the pan-species aldolase antigen by the blood Binax malaria test in FIG. 1. A commercial test for whole blood detection of parasite lactate dehydrogenase, found that none of the urines were positive for this protein in FIG. 2. The antibody in this commercial test kit may recognize only native protein and not be optimal for urine detection.

Figure 7:
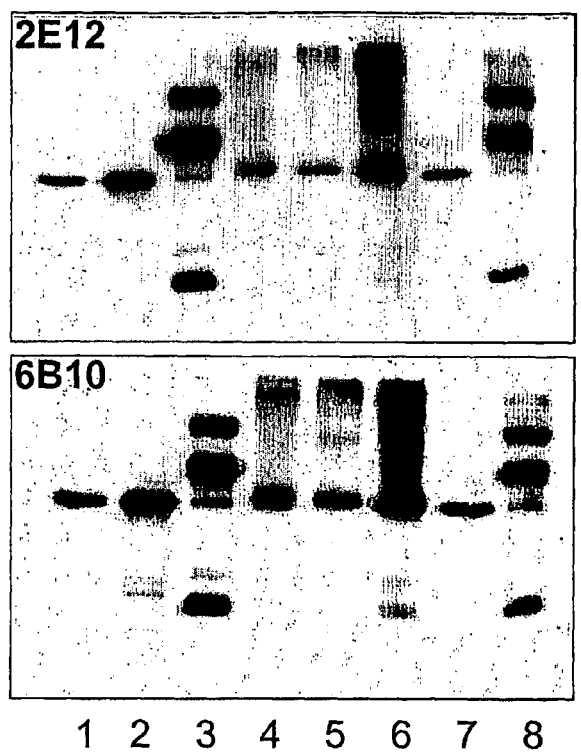
FIG. 7 depicts the probing of two aldolase monoclonal antibodies, 2E12 and 6B10, to *Plasmodium* aldolase from different *Plasmodium* species. Lanes; 1 Pvivax (D19), 2 *P. falciparum* (3D7), 3 *P. yoelii*, 4 *P. knowlesi*, 5. *P. brasilaneum*, 6. *P. ovale*, 7. *P. vivax* (D73), 8. *P. chabaudi*. Lanes 6 and 8 from mouse species also show secondary antibody reactive to heavy and light chains.

A panel of monoclonal antibodies to the antigens detected in the urine were made to verify results outside setting of commercial kits made for blood. Three hybridoma clones were identified, two to HRP II and III and one to a panspecies aldolase. The antibodies detect *P. falciparum* HRP II and III in FIGS. 3-6 and also the pan *Plasmodium* species aldolase in FIG. 7. Sequence of representative protein HRP II and III showing a common AHHAHHAA(D,N) motif (SEQ ID NO: 4) in FIG. 8 and also below.

PfHRP II (SEQ ID NO: 5)
MVSFSKNKVLSAAVFASVLLLDNNNSAFNNNLCSKNAKGLNLNKRLLHET

QAHVDDAHHAHHVADAHHAHHAADAHHAHHAADAHHAHHAADAHHAHHAA

DAHHAHHAAYAHHAHHAADAHHAHHASDAHHAADAHHAAYAHHAHHAADA

HHAHHASDAHHAADAHHAAYAHHAHHAADAHHAADAHHATDAHHAHHAAD

ARHATDAHHAADAHHATDAHHAADAHHAADAHHATDAHHAADAHHATDAH

HAADAHHAADAHHATDAHHAHHAADAHHAAAHHATDAHHATDAHHAAAHH

EAATHCLRH

PfHRP III (SEQ ID NO: 6)
MVSFSKNKILSAAVFASVLLLDNNNSEFNNNLFSKNAKGLNSNKRLLHES

QAHAGDAHHAHHVADAHHAHHAANAHHAANAHHAANAHHAANAHHAANAH

HAANAHHAANAHHAANAHHAANAHHAANAHHAANAHHAANAHHAANAHHA

ANAHHAANAHHAADANHGFHFNLHDNNSHTLHHAKANACFDDSHHDAHHD

GAHHDDAHHDGAHHDDAHHDGAHHDDAHHDGAHHDDAHHDGAHHDGAHHD

GAHHNATTHHLHH

Figure 9:
FIG. 9 depicts Western blot twelve urine samples from individuals infected with *P. falciparum*. Western blot with new monoclonal 3A4 detects pfHRP II in 70% of urines that were not concentrated. Eight out of twelve were positive from 30 μL of urine. Blood in urine-sample 1—only Protein is 1-2+ for all samples.

In FIG. 9 A western blot performed on 12 urine samples from malaria positive subjects detects HRP II with less sensitivity as is known with limit of detection with the Western blot technique.

Example 2

A specific urine designed malaria test (version number 1) was made to detect *P. falciparum* protein HRP II and III and aldolase.

Figure 10:
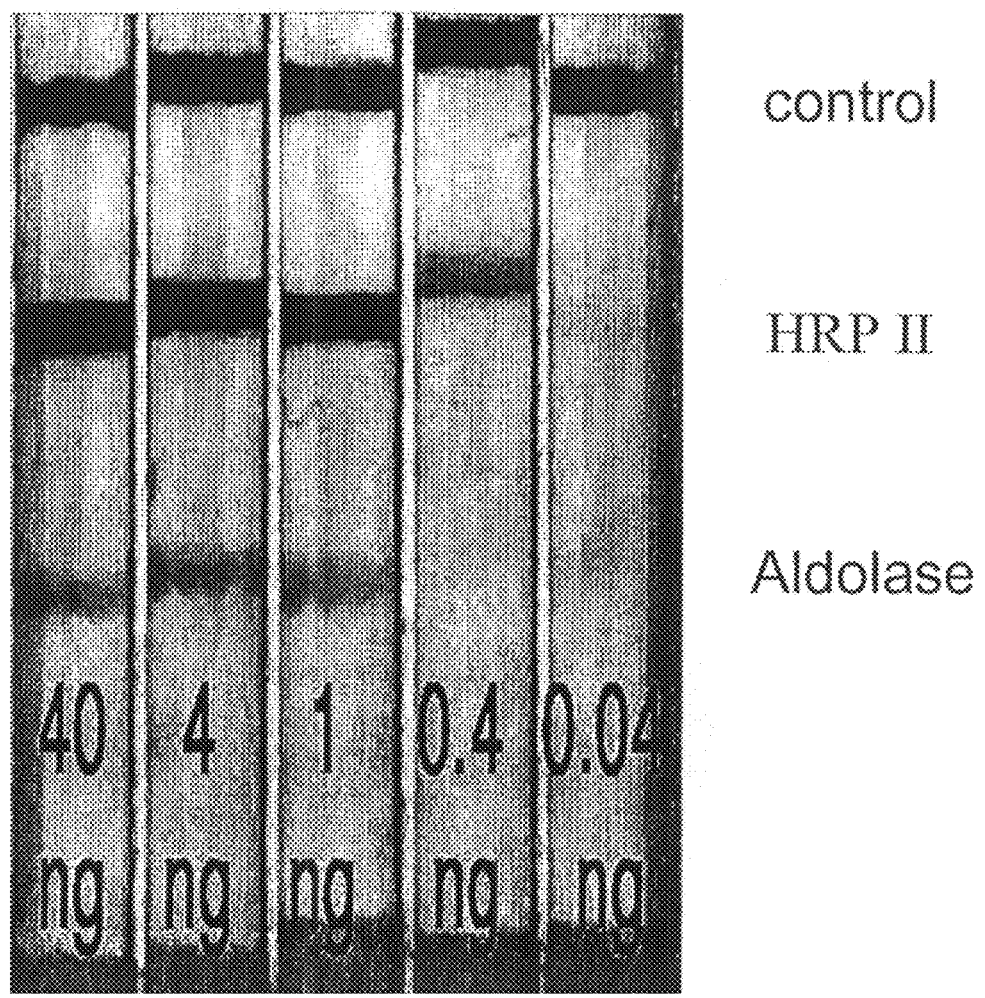
FIG. 10 depicts novel malaria urine dipstick test results for limit of detection. The malaria urine test was able to detect 40 pcg of HRP II in 200 μL of urine. This is about 25-30 times more sensitive than most ICT blood tests, Western Blot or ELISA.

The novel malaria urine tests described herein detects 40 picograms of HRP II in 200 microliters of urine in FIG. 10. Humans filter 180 liters of plasma into kidneys each day which is concentrated into ~liter of urine. Most is resorbed or degraded in kidney lysosomes. Malaria parasitemia=10-100 million infected erythrocytes per ml of blood. A million parasites make about a nanogram of HRP E. A thousand parasites per microliter×5 liter blood volume=5×109 total parasites=5 micrograms of HRP II; 40 parasites per microliter=200 million total parasites=200 nanograms HRP II. Two hundred (200) nanograms per liter is 200 picograms per ml or 20 picograms per 100 microliters. Therefore, the theoretical limit of detection is about 40 parasites per microliter.

ELISAs for HRP II detects about a nanogram of HRP II per 100 microliters. Western blots detects about a nanogram per 50 to 100 microliters. Blood ICT also detect about a nanogram of HRP II. Western Blot and ELISA then would detect 10 nanograms per ml or 10 micrograms per liter. This equals 2,000 parasites per microliter if perfect distribution to urine which is higher than the novel urine malaria test.

Figure 11:
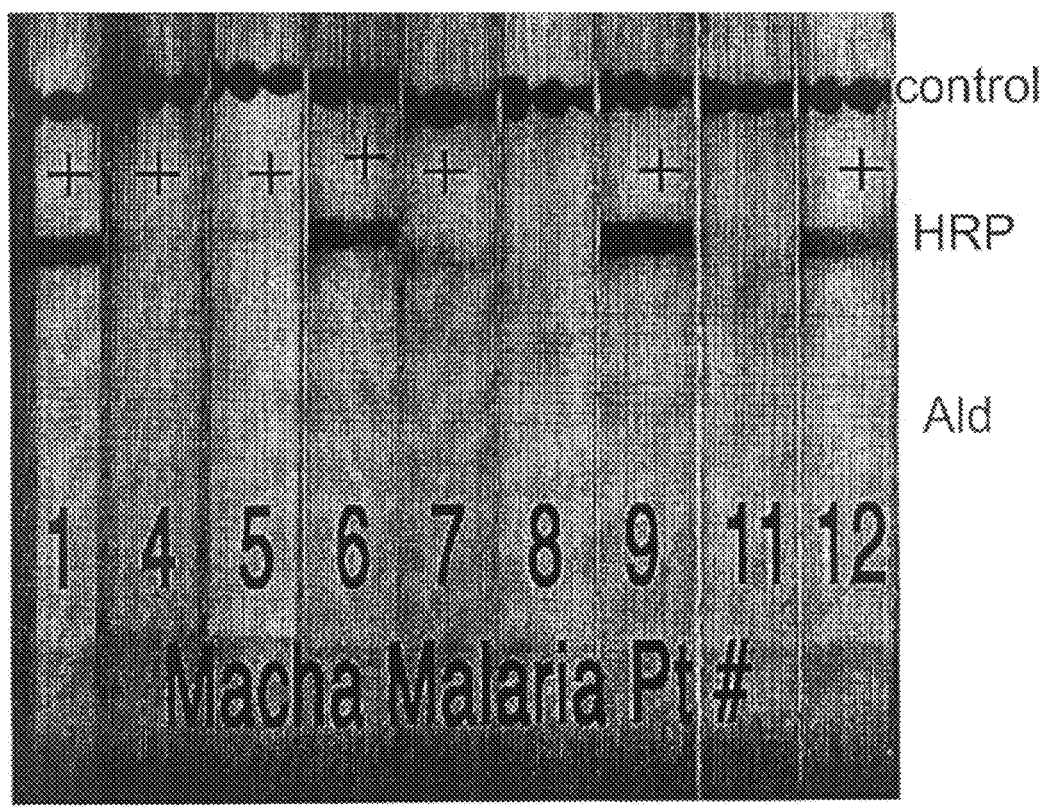
FIG. 11 depicts novel malaria urine dipstick test results on archival frozen samples that were used FIG. 1. Seven of none were positive for HRP II and samples 8 and 11 were still negative.

The previously interrogated frozen urines were tested with the new malaria urine test and show in FIG. 11 that 7 of nine urines are positive for malaria HRP II or III detection.

Example 3

Figure 12:
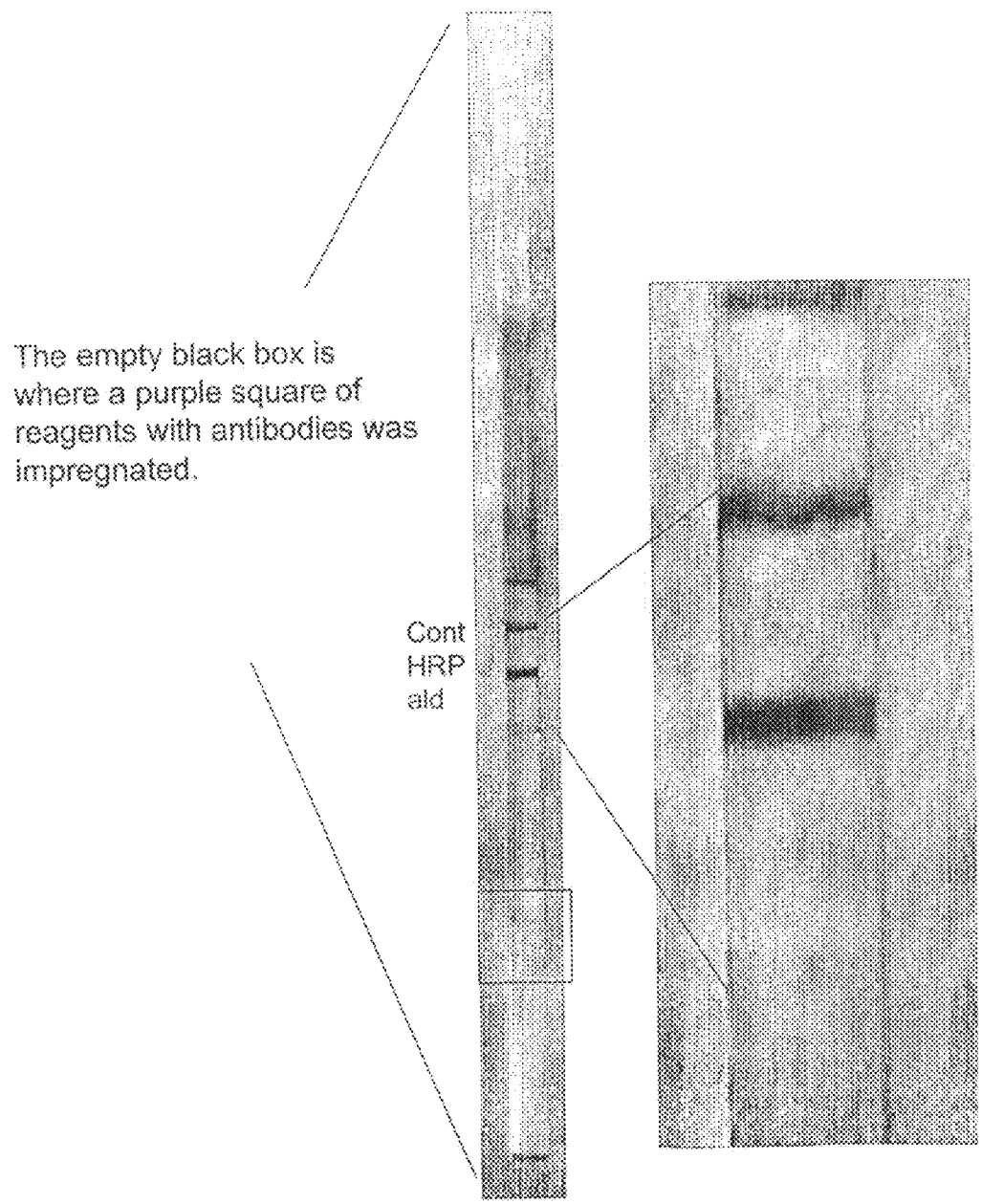
FIG. 12 depicts test results of novel malaria urine dipstick from first positive field sample.
Figure 13:
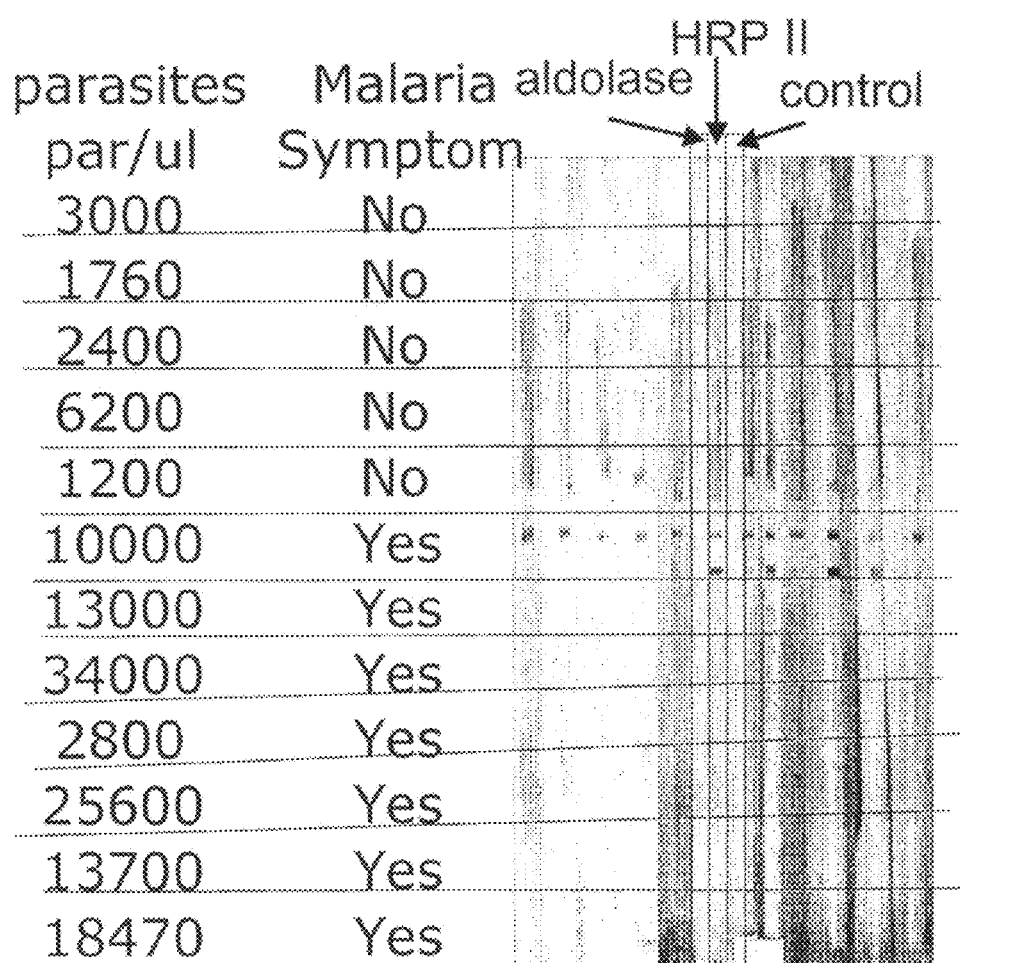
FIG. 13 depicts test results of novel malaria urine dipstick for 12 field patient samples demonstrating that HRP II band is positive in symptomatic patients but negative in asymptomatic patients.

Urine malaria antigen detection was performed on 17 symptomatic children and 23 asymptomatic children (1 adult) in a field study. The symptomatic children presented ill to clinic or hospital. The asymptomatic patients were identified on an active community screen where healthy individuals had blood film read and urine was collected the next day. These individuals despite *P. falciparum* parasites in blood had no symptoms. The immunochromatographic test strip was placed in 200 microliters of urine and results read in 10 minutes with no other manipulations. The first ever positive urine malaria test is shown in FIG. 12. The urine malaria antigen detection was positive in 16 of 17 symptomatic children with confirmed blood film parasitemias, while only 2 of 23 asymptomatic children identified on an active community surveillance screen with confirmed blood films were positive by urine antigen detection as seen in Table 2 and FIG. 13.

TABLE 2

| | | Malaria urine test | | Multistix urine analysis result | | | |
|---|---|---|---|---|---|---|---|
| par/ul | clinical | hrp II | aldolase | blood | prot | pH | spec grav |
| 16/17 positive 88% sensitivity in symptomatic patients | | | | | | | |
| 232800 | Symptomatic | 2 | 0.5 | 3+ | 30 | 6.5 | 1.02 |
| 222153 | Symptomatic | 0.5 | 0 | nil | 30 | 6.5 | 1.01 |
| 188689 | Symptomatic | 1 | 0 | 1+ | nil | 6.5 | 1.01 |
| 89943 | Symptomatic | 1 | 0 | nil | 15 | 6 | 1.03 |
| 84000 | Symptomatic | 0 | 0 | nil | nil | 6 | 1.03 |
| 57900 | Symptomatic | 0.5 | 0 | nil | 1+ | 5 | 1.025 |
| 34000 | Symptomatic | 2 | 1 | 1+ | nil | 5 | 1.01 |
| 25600 | Symptomatic | 2 | 0.5 | nil | nil | 5 | 1.005 |
| 18470 | Symptomatic | 2 | 0 | 2+ | nil | 5 | 1.005 |
| 13700 | Symptomatic | 0.5 | 0 | 3+ | 1+ | 5 | 1.03 |
| 13000 | Symptomatic | 1 | 0.5 | nil | nil | 6 | 1.005 |
| 10000 | Symptomatic | 2 | 0.5 | 1+ | 1+ | 6 | 1.015 |
| 8539 | Symptomatic | 2 | 0.5 | nil | nil | 6 | 1.02 |
| 2800 | Symptomatic | 1 | 0.5 | 1+ | 1+ | 6 | 1.03 |
| 960 | Symptomatic | 2 | 0.5 | nil | 1+ | 6 | 1.005 |
| | Symptomatic | 2 | 0.5 | nil | 30 | 6.5 | 1.03 |
| | Symptomatic | 2 | 0.5 | 1+ | 30 | 6 | 1.03 |
| 2/23 positive in asymptomatic patients = 9% | | | | | | | |
| 17560 | Asymptomatic | 0 | 0 | nil | nil | 8 | 1.01 |
| 13508 | Asymptomatic | 0 | 0 | nil | 100 | 7 | 1.025 |
| 6545 | Asymptomatic | 0 | 0 | nil | nil | 5 | 1.03 |
| 6200 | Asymptomatic | 0 | 0 | 2+ | nil | 7 | 1.005 |
| 5130 | Asymptomatic | 0 | 0 | nil | 0 | 8.5 | 1.005 |
| 3000 | Asymptomatic | 0 | 0 | 3+ | nil | 6 | 1.005 |
| 2400 | Asymptomatic | 0 | 0 | 1+ | nil | 6 | 1.02 |
| 2150 | Asymptomatic | 0 | 0 | nil | nil | 8.5 | 1 |
| 1760 | Asymptomatic | 0 | 0 | 1+ | nil | 6 | 1.025 |
| 1708 | Asymptomatic | 0 | 0 | nil | nil | 5 | 1.03 |
| 1280 | Asymptomatic | 0 | 0 | nil | nil | 8 | 1.005 |
| 1200 | Asymptomatic | 0 | 0 | 1+ | 1+ | 5 | 1.015 |
| 1090 | Asymptomatic | 0 | 0 | 3+ | 200 | 8.5 | 1.005 |
| 731 | Asymptomatic | 0 | 0 | nil | nil | 8.5 | 1.005 |
| 651 | Asymptomatic | 0 | 0 | 3+ | 300 | 8.5 | 1.005 |
| 615 | Asymptomatic | 0 | 0 | nil | nil | 6 | 1.03 |
| 475 | Asymptomatic | 0 | 0 | nil | nil | 6 | 1.03 |
| 456 | Asymptomatic | 0 | 0 | nil | nil | 8.5 | 1.02 |
| 408 | Asymptomatic | 0 | 0 | nil | 30 | 8.5 | 1.005 |
| 385 | Asymptomatic | 1 | 0.5 | nil | 30 | 7 | 1.015 |
| 235 | Asymptomatic | 0 | 0 | nil | 30 | 8.5 | 1.005 |
| 200 | Asymptomatic | 0 | 0 | nil | nil | 7.5 | 1.02 |
| 137 | Asymptomatic | 0.5 | 0 | 1+ | nil | 7 | 1 |

The geometric mean in the symptomatic and asymptomatic children was 22,676 and 1,270 parasites/microliter (ranges-960-232,600 and 137-17,560) respectively. Of the 18 positive urine malaria antigen tests, only 9 were positive for microscopic blood with the Bayer Multistix 10 SG urine dipstick analysis indicating that the urine malaria test works in the absence of detectable hematuria.

Fever by any mechanism increases protein amounts in urine. Many patients with parasites numbers above 1,000 per microliter were negative on urine test in the absence of fever. This would be the first to distinguish symptomatic and asymptomatic parasitemia which present PCR, and blood immunochromatographic tests cannot do.

REFERENCES

All references are hereby incorporated by reference in their entirety.

Altschul S. et al., "Gapped BLAST and PSI-BLAST: a new generation of protein database search programs," *Nucleic Acids Research* 25, 3389-3402 (1997).

*APL Technical Digest*, vol. 20, no. 3, (1999) This volume contains a series of papers dedicated to description of the APL biological weapons detection effort.

Brown, G., Coppel, R., Vrbova, H., Grummont, R., and Anders R., "*P. falciparum*: comparative analysis of erythrocyte stage-dependent protein antigens," *Exp. Parasitology* 53, 279-84 (1982).

Cohen, S. and Chait, B., "Mass Spectrometry of Whole Proteins Eluted from SDS-PAGE Electrophoresis Gels," *Analytical Biochemistry* 247, 257-267 (1997).

Cornish, T. and Bryden, W., "Miniature Time-of-Flight Mass Spectrometer for a Field-Portable Biodetection system," *APL Tech. Digest* 20, 335-341 (1999).

Cowman, A., "Functional analysis of drug resistance in *Plasmodium falciparum* in the post-genomic era," *Int. J. Parasitol*. 31, 871-8 (2001).

Dennis, V "Investigations of renal function" in *Cecil Textbook of Medicine* eds Wyngaarden, J, Smith, L and Bennett, C 492-499 (1988)

Fenton, B., Walker, A. and Walliker, D., "Protein variation in clones of *P. falciparum*: detected by 2-D electrophoresis," *Mol. Biochem. Parasitology* 16, 173-83 (1985).

Gardner, M. et al., "Chromosome 2 Sequence of the Human Malaria Parasite *P. falciparum*," *Science* 282, 1126-1132 (1998).

Genton, B., Paget, S., Beck, H., Gibson, N., Alpers, M. and Hii, J., "Diagnosis of *Plasmodium Falciparum* Infection Using Parasight-F Test in Blood and Urine of Papua New Guinean Children," *Southeast Asian J. Tropical Medicine Public Health* 29, 35-40 (1998).

Gobom, J., Nordhoff, E., Mirgorodskaya, Ekman, R. and Roepstorff, P., "Sample Purification and Preparation Technique Based on Nano-Scale Reverse-Phase Columns for the Sensitive Analysis of Complex Peptide Mixtures by MALDI-MS," *J. Mass Spectrometry* 34, 105-116 (1999).

Godovac-Zimmermann, J and Brown, L., "Perspectives for Mass Spectrometry and Functional Proteomics," *Mass Spectrometry Reviews* 20, 1-57 (2001).

Hodder, A., Crewther, P., Matthew, M., Reid, G., Moritz, R. et al. "The Disulfide Bond Sturcture of *Plasmodium* Apical Membrane Antigen-1," *J. Biological Chemistry* 271 29446-29452 (1996).

Howell, S., Withers-Martinez, Kocken, C., Thomas, A. and Blackman, M., "Proteolyitic Processing and the Primary Structure of *P. falciparum* Apical Membrane Antigen-1," *J, of Biological Chemistry*, 276, 31311-31320 (2001).

Hurst, G., Buchanan, M., Foote, L. and Kennel, S., "Analysis for TNF-☐ Using Solid Phase Affinity Capture with Radiolabel and MALDI-MS detection," *Analytical Chemistry* 71, 4727-2733 (1999).

Kappe, S. et al., "Exploring the Transcriptome of the Malaria Sporozoitre Stage," *Proc. Natl. Academy Sci USA* 98, 9895-9900 (2001).

Karas, M., Bachmann, D., Hillenkamp, F., "Influence of the Wavelength in High-Irradiance UV Laser Desorption Mass Spectrometry of Organic Molecules," *Analytical Chemistry* 57, 2935-2939 (1985).

Karas, M., Bachmann, D., Bahr, U., and Hillenkamp, F., "Matrix-Assisted Ultraviolet Laser Desorption of Non-volatile Compounds," *International Journal of Mass Spectrometry Ion Processes* 78, 53-68 (1987).

Karas, M and Hillenkamp, F., "Laser Desorption of Proteins with Molecular Masses Exceeding 10 kDa," *Analytical Chemistry* 60, 2299-2301 (1988).

Katzin, A., Kimura, E., Alexandre, C. and Val Ramos, A., "Detection of Antigens in Urine of Patients with Acute *Falciparum* and *Vivax* Malaria Infections," *Am. J. Trop. Med. Hyg.* 45, 453-462 (1991).

Keough T., Youngquist, R. and Lacey, M., "A method for high sensitivity peptide sequencing using postsource decay MALDI-MS," *Proc. Natl. Academy Sci. USA* 96, 7131-7136 (1999).

Kussmann, M., Nordhoff, E., Rahbek-Nielsen, H., Haebel, S., Rossel-Larsen M. et al., "MALDI-MS Sample Preparation Techniques Designed for Various Peptide and Protein Analytes," *J. Mass Spectrometry* 32, 593-601 (1997).

Militao, D. N., Camargo, L. M., Katzin, A. M., "Detection of Antigens in the Urine of Patients with Acute *Plasmodium vivax* Malaria," *Experimental Parasitology* 76, 115-120 (1993).

Nelson, R., Jarvik, J., Taillon, B. and Tubbs, K., "BIA/MS of Epitope-Tagged Peptides Directly from *E. coli* Lysate: Multiplex Detection and Protein Identification at Low-Femtomole to Subfemtomole Levels," *Analytical Chemistry* 71, 2858-2865 (1999).

Neubauer G., King, A., Rappsilber, J., Calvio, C., Watson, M., Ajuh, P., Sleeman, J., Lamond, A. and Mann, M., "Mass spectrometry and EST-database searching allows characterization of the multi-protein spliceosome complex," *Nature Genetics* 20, 46-50 (1998).

Pachebat, J., Ling. I., Grainger, M., Trucco, C. et al., "The 22 kDa component of the protein complex on the surface of *P. falciparum* merozoites is derived from a larger precursor, merozoite surface protein 7," *Molecular & Biochemical Parasitology* 117, 83-89 (2001).

Pandey, A. and Mann, M., "Proteomics to study genes and genomes," *Nature* 405, 837-846 (2000).

Peter, J., Unverzagt, C., Lenz, H. and Hoesel, W., "Purification of Prostate-Specific Antigen from Human Serum by Indirect Immunosorption and Elution with a Hapten," *Analytical Biochemistry* 273, 98-104 (1999).

Pinswasdi C., Thaithong, S., Beale, G., Fenton, B., Webster, H. and Pavanand, K., "Polymorphism of proteins in malaria parasites following mefloquine treatment," *Mol. Biochem. Parasitol.* 23, 159-64 (1987).

Qian, X., Zhou, W., Khaledi, M. and Tomer, K., "Direct analysis of the products of sequential cleavages of peptides and proteins affinity bound to immobilized metal ion beads by MALDI-TOF-MS," *Analytical Biochemistry* 274, 174-180 (1999).

Rabilloud, T., Blisnick, T., Heller, M., Luche S., Aebersold, R., Lunardi, J. and Braun-Breton, C. "Analysis of membrane proteins by two-dimensional electrophoresis: Comparison of the proteins extracted from normal or *P. falciparum* infected erythrocyte ghosts," *Electrophoresis* 20, 3603-3610 (1999).

Rodriguez-Del Valle, M., Quakyi, I. A., Amuesi, J., Quaye, J. T., Nkrumah, F. K. and Taylor, D., "Detection of Antigens and Antibodies in the Urine of Humans with *Plasmodium falciparum* Malaria," *J. Clin. Microbiology* 29, 1236-1242 (1991).

Sagoe-Moses, C Pearson, R Perry, J and Jagger, J "Risks to Healthcare Workers in Developing Countries" *New Eng. J Med.* 345:538-541 (2001)

Schriemer, D. and Li, L., "Combining Avidin-Biotin Chemistry with MALDI-MS," *Analytical Chem.* 68, 3382-3387 (1996).

Seesod, N., Lunderberg, J., Hedrum, A., Aslund, L., Holder, A., Thaithong, S. and Uhlen, M., Immunomagnetic purification to facilitate DNA diagnosis of *P. falciparum*," *J. Clin. Microbiology* 31, 2715-9 (1993).

Sherman, I "Carbohydrate Metabolism of Asexual Stages" in *Malaria* ed Sherman, I p 575 ASM (1998)

Shevchenko, A., Jensen, O., Podtelejnikov, et al., "Linking genome and proteome by mass spectrometry: Large scale identification of yeast proteins from two dimensional gels," *Proc. Natl. Academy Science USA* 93, 14440-14445 (1996a)

Shevchenko, A., Wilm, M., Vorm, O. and Mann, M., "Mass Spectrometric Sequencing of Proteins from Silver-Stained Polyacrylamide Gels," *Analytical Chemistry* 68, 850-858 (1996b).

Spengler, B. "Post-source Decay Analysis in MALDI-MS of Biomolecules," *J. Mass Spectrometry* 32, 1019-1036 (1997).

Tait, A. "Analysis of protein variation in *P. falciparum* by 2D electrophoresis," *Mol. Biochem. Parasitology* 2, 205-218 (1981).

Wilkins, M., *Proteome Research: New Frontiers in Functional Genomics*, eds. Wilkins, M. R., Williams, K. L, Appel, R. D. and Hochstrasser, D. F., Springer-Verlag, Heidelberg, Germany (1997).

Ethiop Med J. 1984 Jul.; 22(3):119-27. Detection of malaria antigens in urine, using a solid-phase radioimmunoassay: preliminary study.

Am J Trop Med Hyg. 1991 October; 45(4):453-62. Detection of antigens in urine of patients with acute *falciparum* and *vivax* malaria infections.

Exp Parasitol. 1993 March; 76(2):115-20 Detection of antigens in the urine of patients with acute *Plasmodium vivax* malaria.

Southeast Asian J Trop Med Public Health. 1998 Mar.; 29(1):35-40. Diagnosis of *Plasmodium falciparum* infection using ParaSight(R)-F test in blood and urine of Papua New Guinean children.

J Travel Med. 1996 Sep. 1; 3(3):172-173. Rapid Manual Diagnosis of *Plasmodium falciparum* Malaria Using ParaSight-F Dipsticks Applied to Human Blood and Urine.

J Clin Microbiol. 1991 Jun.; 29(6):1236-42. Detection of antigens and antibodies in the urine of humans with *Plasmodium falciparum* malaria Mu J, Duan J, Makova K D, Joy D A, Huynh C Q, Branch O H, Li W H, Su X Z. Chromosome-wide SNPs reveal an ancient origin for *Plasmodium falciparum*. Nature. 2002; 418:323-6, describes *P. falciparum* from all over the world with a tree showing genetic distance between strains.

---

What is claimed is:

1. A method of diagnosing a *Plasmodium falciparum* infection in a human subject using an immunoassay, the method comprising contacting a urine sample obtained from the subject with the monoclonal antibody 3A4 deposited as PTA-123432 or the monoclonal antibody 4A5 deposited as PTA-123433, wherein the monoclonal antibody binds to histidine rich protein II (HRP II) and/or HRP III of *Plasmodium falciparum* and detects the presence of the HRP II and/or the HRP III in the urine, thereby diagnosing the *Plasmodium falciparum* infection in the human subject.

2. The method of claim 1, wherein the urine sample is buffered to a pH of between 4 and 9.

3. The method of claim 1, wherein the urine sample is buffered to a pH of 7.5 to 8.5.

4. The method of claim 1, wherein the immunoassay is selected from one or more of Western blot, ELISA, immunoprecipitation, immunodiffusion, radioimmunoassay, immunofluorescence, or lateral flow assay.

* * * * *

SEQUENCE LISTING

```
<160> NUMBER OF SEQ ID NOS: 8

<210> SEQ ID NO 1
<211> LENGTH: 8
<212> TYPE: PRT
<213> ORGANISM: Plasmodium falciparum

<400> SEQUENCE: 1

Ala His His Ala His His Ala Ala
1               5

<210> SEQ ID NO 2
<211> LENGTH: 6
<212> TYPE: PRT
<213> ORGANISM: Plasmodium falciparum

<400> SEQUENCE: 2

Ala His His Ala Ala Asp
1               5

<210> SEQ ID NO 3
<211> LENGTH: 9
<212> TYPE: PRT
<213> ORGANISM: Plasmodium falciparum

<400> SEQUENCE: 3

Ala His His Ala His His Ala Ala Asp
1               5

<210> SEQ ID NO 4
<211> LENGTH: 9
<212> TYPE: PRT
<213> ORGANISM: Plasmodium falciparum
<220> FEATURE:
<221> NAME/KEY: MOD_RES
<222> LOCATION: (9)..(9)
<223> OTHER INFORMATION: Asp or Asn

<400> SEQUENCE: 4

Ala His His Ala His His Ala Ala Xaa
1               5

<210> SEQ ID NO 5
<211> LENGTH: 309
<212> TYPE: PRT
<213> ORGANISM: Plasmodium falciparum

<400> SEQUENCE: 5

Met Val Ser Phe Ser Lys Asn Lys Val Leu Ser Ala Ala Val Phe Ala
1               5                   10                  15

Ser Val Leu Leu Leu Asp Asn Asn Asn Ser Ala Phe Asn Asn Asn Leu
            20                  25                  30

Cys Ser Lys Asn Ala Lys Gly Leu Asn Leu Asn Lys Arg Leu Leu His
```

```
            35                  40                  45
Glu Thr Gln Ala His Val Asp Asp Ala His Ala His His Val Ala
 50                  55                  60
Asp Ala His His Ala His His Ala Ala Asp Ala His Ala His His
 65                  70                  75                  80
Ala Ala Asp Ala His His Ala His His Ala Ala Asp Ala His His Ala
                 85                  90                  95
His His Ala Ala Asp Ala His His Ala His Ala Ala Tyr Ala His
                100                 105                 110
His Ala His His Ala Ala Asp Ala His His Ala His His Ala Ser Asp
                115                 120                 125
Ala His His Ala Ala Asp Ala His His Ala Tyr Ala His His Ala
130                 135                 140
His His Ala Ala Asp Ala His His Ala His Ala Ser Asp Ala His
145                 150                 155                 160
His Ala Ala Asp Ala His His Ala Ala Tyr Ala His His Ala His His
                165                 170                 175
Ala Ala Asp Ala His His Ala Asp Ala His His Ala Thr Asp Ala
                180                 185                 190
His His Ala His His Ala Ala As

```
Ala Asn Ala His His Ala Asn Ala His Ala Ala Asn Ala His
            100                 105                 110

His Ala Ala Asn Ala His His Ala Ala Asn Ala His His Ala Ala Asn
        115                 120                 125

Ala His His Ala Ala Asn Ala His His Ala Ala Asn Ala His His Ala
    130                 135                 140

Ala Asn Ala His His Ala Ala Asn Ala His His Ala Ala Asn Ala His
145                 150                 155                 160

His Ala Ala Asp Ala Asn His Gly Phe His Phe Asn Leu His Asp Asn
                165                 170                 175

Asn Ser His Thr Leu His His Ala Lys Ala Asn Ala Cys Phe Asp Asp
            180                 185                 190

Ser His His Asp Asp Ala His His Asp Gly Ala His His Asp Asp Ala
        195                 200                 205

His His Asp Gly Ala His His Asp Asp Ala His His Asp Gly Ala His
    210                 215                 220

His Asp Asp Ala His His Asp Gly Ala His His Asp Asp Ala His His
225                 230                 235                 240

Asp Gly Ala His His Asp Gly Ala His His Asp Gly Ala His His Asn
                245                 250                 255

Ala Thr Thr His His Leu His His
            260
```

<210> SEQ ID NO 7
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Ala His His Ala His His Ala Ala Asp Ala His His Ala His His Ala
1               5                   10                  15

Ala Asp Ala His His Ala His His Ala Ala Asp Ala His His Ala His
            20                  25                  30

His Ala Ala Asp Ala His His Ala His His Ala Ala Asp Ala His His
        35                  40                  45

Ala His His Ala Ala Asp Ala His His Ala His His Ala Ala Asp Ala
    50                  55                  60

His His Ala His His Ala Ala Asp Ala His His Ala His His Ala Ala
65                  70                  75                  80

Asp Ala His His Ala His His Ala Ala Asp
                85                  90
```

<210> SEQ ID NO 8
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Ala His His Ala His His Ala Ala Asn Ala His His Ala His His Ala
1               5                   10                  15

Ala Asn Ala His His Ala His His Ala Ala Asn Ala His His Ala His
            20                  25                  30
```

-continued

```
His Ala Ala Asn Ala His His Ala His His Ala Ala Asn Ala His His
             35              40              45
Ala His His Ala Ala Asn Ala His His Ala His His Ala Ala Asn Ala
         50              55              60
His His Ala His His Ala Ala Asn Ala His His Ala His His Ala Ala
65              70              75              80
Asn Ala His His Ala His His Ala Ala Asn
             85              90
```